US011307184B2

(12) United States Patent
Lim et al.

(10) Patent No.: US 11,307,184 B2
(45) Date of Patent: Apr. 19, 2022

(54) SENSOR ARRAYS WITH NUCLEOPHILIC INDICATORS

(71) Applicant: iSense LLC, Mountain View, CA (US)

(72) Inventors: Sung Hyun Lim, Mountain View, CA (US); Autumn Maruniak, Sunnyvale, CA (US); Nuria Queralto Gratacos, Redwood City, CA (US)

(73) Assignee: iSense LLC, Mountain View, CA (US)

( * ) Notice: Subject to any disclaimer, the term of this patent is extended or adjusted under 35 U.S.C. 154(b) by 97 days.

(21) Appl. No.: 15/897,403

(22) Filed: Feb. 15, 2018

(65) Prior Publication Data

US 2018/0231513 A1    Aug. 16, 2018

Related U.S. Application Data

(60) Provisional application No. 62/459,795, filed on Feb. 16, 2017.

(51) Int. Cl.
| | |
|---|---|
| *G01N 31/22* | (2006.01) |
| *G01N 21/78* | (2006.01) |
| *G01N 33/497* | (2006.01) |
| *G01N 33/569* | (2006.01) |
| *G01N 33/574* | (2006.01) |
| *G01N 21/77* | (2006.01) |

(52) U.S. Cl.
CPC ............ *G01N 31/22* (2013.01); *G01N 21/78* (2013.01); *G01N 33/497* (2013.01); *G01N 33/56911* (2013.01); *G01N 33/574* (2013.01); *G01N 33/57419* (2013.01); *G01N 2021/7793* (2013.01); *G01N 2430/00* (2013.01); *G01N 2800/26* (2013.01)

(58) Field of Classification Search
CPC ...... G01N 31/22; G01N 21/78; G01N 33/497; G01N 33/56911; G01N 33/574; G01N 33/57419
USPC ........................................................ 422/165
See application file for complete search history.

(56) References Cited

U.S. PATENT DOCUMENTS

| | | | |
|---|---|---|---|
| 5,232,839 | A | 8/1993 | Eden |
| 6,369,558 | B2 | 4/2002 | Suslick et al. |
| 6,495,102 | B1 | 12/2002 | Suslick et al. |
| 6,903,823 | B1 | 6/2005 | Mueller |
| 7,261,857 | B2 | 8/2007 | Suslick et al. |
| 7,531,319 | B2 | 5/2009 | Martin et al. |
| 8,617,874 | B2 | 12/2013 | Martin et al. |

(Continued)

FOREIGN PATENT DOCUMENTS

WO    WO-9712994 A1 *  4/1997  ............. C07H 15/26

OTHER PUBLICATIONS

Li. Z. et al. (2011). "Chromo-fluorogenic detection of aldehydes with rhodamine based sensor featuring an intramolecular deoxylactam." Org. Biomol. Chem. 9, 7652-7654. (Year: 2011).*

(Continued)

*Primary Examiner* — Benjamin R Whatley
*Assistant Examiner* — Jacqueline Brazin
(74) *Attorney, Agent, or Firm* — Nixon Peabody LLP

(57) ABSTRACT

Sensors arrays that include indicators arranged in a pattern on a substrate. The indicators include nucleophilic indicators. In some examples, the sensor arrays with multiple nucleophilic indicators provide superior detection and identification of microorganisms, cancer biomarkers, formaldehyde, organophosphates, and aldehydes.

18 Claims, 14 Drawing Sheets

(56) References Cited

U.S. PATENT DOCUMENTS

| | | |
|---|---|---|
| 2003/0143112 A1 | 7/2003 | Suslick et al. |
| 2003/0166298 A1 | 9/2003 | Suslick et al. |
| 2004/0157281 A1 | 8/2004 | Hulkower et al. |
| 2005/0171449 A1 | 8/2005 | Suslick et al. |
| 2006/0073483 A1 | 4/2006 | White |
| 2008/0050839 A1 | 2/2008 | Suslick et al. |
| 2008/0199904 A1* | 8/2008 | Suslick .................... C12Q 1/04 435/34 |
| 2010/0166604 A1* | 7/2010 | Lim ..................... G01N 21/253 422/400 |
| 2013/0096030 A1 | 4/2013 | Jeppesen |
| 2013/0251594 A1* | 9/2013 | Lobnik ................. G01N 21/64 422/82.08 |
| 2015/0099694 A1 | 4/2015 | Lim |
| 2016/0282352 A1* | 9/2016 | Martino ........... G01N 33/57488 |

OTHER PUBLICATIONS

Pararosaniline. Wikipedia. Page was last edited Jan. 13, 2021. (Year: 2021).*

Supplementary European Search Report in European Patent Application No. EP 18754344.2, dated Feb. 26, 2021 (9 pages).

* cited by examiner

SENSOR ARRAYS WITH NUCLEOPHILIC INDICATORS

CROSS-REFERENCE TO RELATED APPLICATIONS

This application claims priority to and the benefit of U.S. Provisional Patent Application No. 62/459,795, filed Feb. 16, 2017 and entitled "Sensor Arrays with Nucleophilic Indicators," the contents of which are hereby incorporated by reference in their entirety as if fully set forth herein.

FIELD

This disclosure relates to artificial noses for the detection of analytes.

BACKGROUND

Array-based sensors mimic the mammalian gustatory and olfactory systems to detect and characterize fluidic samples by measuring a unique composite response for each analyte rather than an analyte specific sensor. Such cross-responsive sensor arrays have been implemented both as an artificial nose technology for the detection of vapors and gases, and as electronic tongue technology for the detection of liquid analytes. Examples include, but not limited to: colorimetric sensor array, conductive polymer or conductive polymer composite arrays, mass sensitive piezoelectric sensors, surface acoustic wave (SAW) transducers, quartz crystal microbalances, functionalized carbon nanotubes and gold nanoparticles based sensors.

Initial work in the field of artificial noses was conducted by Wilkens and Hatman in 1964, though the bulk of research done in this area has been carried out since the early 1980's. See, e.g., W. F. Wilkens and J. D. Hartman, Ann. N.Y. Acad. Sci., 116, 608 (1964); K. Pursaud and G. H. Dodd, Nature, 299, 352-355 (1982); and J. W. Gardner and P. N. Bartlett, Sens. Actuators, B, 18, 210-211 (1994). Vapor-selective detectors or "artificial noses" are typically based upon the production of an interpretable signal or display upon exposure to a vapor-emitting substance or odorant (hereinafter sometimes referred to as an "analyte"). More specifically, typical artificial noses are based upon selective chemical binding or an interface between a detecting element of the artificial nose and an analyte or odorant, and then transducing of that chemical binding into a signal or display, i.e., signal transduction.

Conductive polymer composite arrays have been used for artificial noses. That is, a series of chemically-diverse polymers or polymer blends are chosen so that their composite response distinguishes a given odorant or analyte from others. Examples of polymer array vapor detectors, including conductive polymer and conductive polymer/carbon black composites, are discussed in: M. S. Freund and N. S. Lewis, Proc. Natl. Acad. Sci., U.S.A. 92, 2652-2656 (1995); B. J. Doleman, R. D. Sanner, E. J. Severin, R. H. Grubbs, N. S. Lewis, Anal. Chem., 70, 2560-2564 (1998); T. A Dickinson, J. White, J. S. Kauer, D. R. Walt, Nature, 382, 697-700 (1996) (polymer array with optical detection); A. E. Hoyt, A. J. Ricco, H. C. Yang, R. M. Crooks, J. Am. Chem. Soc., 117, 8672-8673 (1995); and J. W. Grate and M. H. Abraham, Sens. Actuators, B, 3, 85-111 (1991).

Other sensing materials include functionalized self-assembled monolayers (SAM), metal oxides, and dendrimers. Signal transduction is commonly achieved with mass sensitive piezoelectric substrates, surface acoustic wave (SAW) transducers, or conductive materials. Optical transducers (based on absorbance or luminescence) have also been examined. Examples of metal oxide, SAM, and dendrimer-based detectors are discussed in J. W. Gardner, H. V. Shurmer, P. Corcoran, Sens. Actuators, B, 4, 117-121 (1991); J. W. Gardner, H. V. Shurmer, T. T. Tan, Sens. Actuators, B, 6, 71-75 (1992); and R. M. Crooks and A. J. Ricco, Acc. Chem. Res., 31, 219-227 (1998).

Techniques have also been developed using metalloporphyrins for optical detection of a specific, single gas such as oxygen or ammonia, and for vapor detection by chemically interactive layers on quartz crystal microbalances. See, A. E. Baron et al., Rev. Sci. Instrum., 64, 3394-3402 (1993); J. Kavandi et al., Rev. Sci. Instrum., 61, 3340-3347 (1990); W. Lee, et al., J. Mater. Chem., 3, 1031-1035 (1993); A. A. Vaughan, M. G. Baron, R. Narayanaswamy, Anal. Comm., 33, 393-396 (1996); J. A. J. Brunink, et al., Anal. Chim. Acta, 325, 53-64 (1996); C. DiNatale, et al., Sens. Actuators, B, 44, 521-526 (1997); and C. DiNatale, et al., Mat. Sci. Eng. C, 5, 209-215 (1998).

Other techniques include functionalized carbon nanotubes integrated into a transistor. See, DNA-Decorated Carbon Nanotubes for Chemical Sensing by C. Staii and A. T. Johnson, Nano Lett. 5, 1774-1778 (2005); and functionalized gold nanoparticles based sensor by G. Peng et al., Nat. Nanotechnol. 4, 669-673 (2009). Also, see nanomaterial-based sensors for detection of disease by volatile organic compounds by Y. Y. Broza and H. Haick Nanomedicine, 8, 785-806 (2013); and Sniffing the Unique "Odor Print" of Non-Small-Cell Lung Cancer with Gold Nanoparticles by O. Barash, N. Peled, F. R. Hirsch, H. Haick, Small, 5, 2618-2624 (2009).

Artificial noses based on colorimetric sensor arrays exist that are capable of detecting volatile organic compounds (VOCs) at low concentrations and a high degree of accuracy. Colorimetric sensor arrays that are capable of detecting VOCs typically contain chemically responsive indicators that change color when VOCs contact the indicator molecules. The sensing elements of the array, chromogenic indicators, are immobilized in host materials to protect and support the indicators onto a solid substrate. Colorimetric sensor arrays are typically immobilized in organically modified silanes (ormosils) or polymers. For dye-based sensor arrays based on a semi-fluidic polymer, see U.S. Pat. No. 6,368,558, issued on Apr. 9, 2002 and titled "Colorimetric Artificial Nose Having an Array of Dyes and Method for Artificial Olfaction" by K. S. Suslick and N. A. Rakow. This technology uses molecular indicators solvated in semi-fluidic plasticizers and porous films to make the colorimetric sensor array. There are a several drawbacks to using this method for many indicators used in the colorimetric sensor array. The printed dyes are solvated in a semi-fluidic plasticizer, so the dyes may be unstable and leach into analyte solutions, resulting in limited shelf-life and operational life. More recently, nanoporous pigment based colorimetric sensor array have been reported to immobilize the indicators in sol-gel matrices. This sol-gel approach allows customized sol-gel matrices with a range of hydrophobicity, porosity and surface area. However, this sol-gel technique does not work with all indicators due to their intrinsic solubility or pH requirement. For more details, see an Optoelectronic Nose for the Detection of Toxic Gases by S. H. Lim et al., Nat. Chem., 1, 562-567 (2009).

SUMMARY

The present invention comprises a colorimetric sensor array comprised of indicators immobilized in various host materials, which in combination provides improved colorimetric sensor arrays for detecting and identifying various fluidic analytes in both liquid and vapor phase. In particular, the invention provides an optimal host material for each indicator to enhance the array sensitivity and improve the shelf-life of the array.

In one aspect, the invention provides a colorimetric sensor array include a substrate, a first spot on the substrate and a second spot on the substrate. The first spot includes a first indicator immobilized in a first host material. The second spot includes a second indicator that may include a second host material. The composition of the first spot is different from the second spot, which may differ in the indicator and/or the host material.

In another aspect, the invention provides a method of detecting analyte in a sample, including obtaining a first image of the colorimetric sensor array in the absence of the analyte, obtaining a second image of the colorimetric sensor array in the presence of the analyte, and analyzing a color difference between the first image and the second image. The resulting pattern of color change manifested by the sensor array is indicative of a specific or given analyte.

In one embodiment, a sensor array comprises a first and second indicator deposited on a substrate in a predetermined pattern. The first and second indicators can be nucleophilic indicators that have a distinct spectral response to at least one distinct analyte.

The at least one distinct analyte can be in a solution when the first and second indicators are exposed to the analyte. Both indicators have a distinct spectral response to this analyte. Alternatively, the at least one distinct analyte can be a volatile organic compound or mixtures of volatile organic compounds. The at least one distinct analyte can also be any one of, or a combination of, the following: a cancer biomarker, an aldehyde, an organophosphate, an electrophilic analyte, and a keytone.

The first and second indicator demonstrate a distinct spectral response when exposed to any of those possible analytes. The response can be in an ultraviolet range.

The first and second indicator can have a nucleophilic die comprised of a plasticizer, a sol-gel, or a polymer.

In another embodiment, the present disclosure provides a method of detecting an analyte. The method comprises first providing a sensor array which comprises a first and second indicator deposited on a substrate in a predetermined pattern. The first and second indicators are nucleophilic indicators and have a distinct spectral response to distinct analytes. Then the method comprises exposing the sensor array to the analyte and detecting a spectral response after exposing the sensor array to the analyte. The method then comprises correlating the spectral response to the presence of the analyte.

In performing this method, the analyte can be a volatile organic compound. The analyte can also be in a solution when it is exposed to the sensor array. Alternatively, when the sensor array is exposed to the analyte, the sensor array can be exposed to a gas that contains the analyte. The analyte in the gas can be a volatile organic compound. In another embodiment, when the sensor array is exposed to the analyte, the sensor array can be exposed to a liquid that contains the analyte.

The spectral response of the sensor array to the analyte can be in an ultraviolet range.

In another embodiment, the present disclosure provides for a sensor array comprising a first indicator and a second indicator deposited on a substrate in a predetermined pattern. The first and second indicators comprise nucleophilic indicators.

In another embodiment, the present disclosure provides for a method of determining if a patient has a malady. The method comprises first providing a sensor array, wherein the sensor array comprises a first indicator and a second indicator deposited on a substrate in a predetermined pattern. The first and second indicators are nucleophilic indicators. Then the method comprises exposing the sensor array to a sample from a patient. Then the method comprises detecting a spectral response after exposing the sensor array to the sample. This response is correlated to the spectral response that shows in the presence of a malady.

The malady can be any one of, or a combination of, the following: cancer, colon cancer, and sepsis. The sample can be the exhaled breath of a patient. The sample can also be a urine sample. Additionally, exposing the sensor array to a sample from the patient can comprise exposing the sensor array to the headspace gas of a blood sample.

BRIEF DESCRIPTION OF DRAWINGS

The accompanying drawings, which are incorporated in and constitute a part of this specification, exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

FIG. 5A depicts an example sensor array prior to exposure to an analyte. FIG. 5B depicts an example sensor array after exposure to an analyte. FIG. 5C depicts an illustration of a difference map (not based on actual sample).

Figure 1:
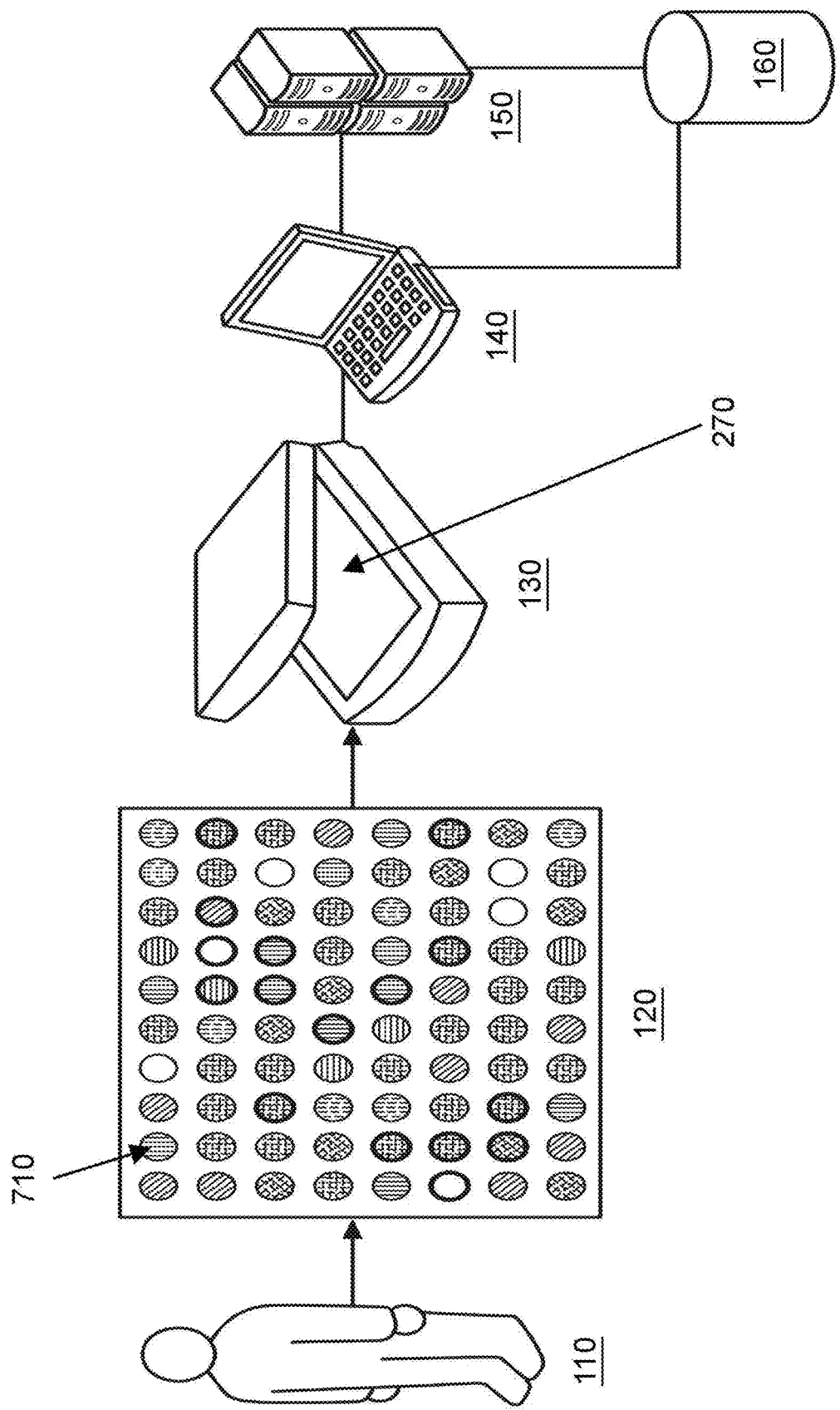
FIG. 1 depicts an example diagram of a system for detecting an array response.

In the drawings, the same reference numbers and any acronyms identify elements or acts with the same or similar structure or functionality for ease of understanding and convenience. To easily identify the discussion of any particular element or act, the most significant digit or digits in a reference number refer to the Figure number in which that element is first introduced.

DETAILED DESCRIPTION

Unless defined otherwise, technical and scientific terms used herein have the same meaning as commonly understood by one of ordinary skill in the art to which this invention belongs. Szycher's Dictionary of Medical Devices CRC Press, 1995, may provide useful guidance to many of the terms and phrases used herein. One skilled in the art will recognize many methods and materials similar or equivalent to those described herein, which could be used in the practice of the present invention. Indeed, the present invention is in no way limited to the methods and materials specifically described.

In some embodiments, properties such as dimensions, shapes, relative positions, and so forth, used to describe and claim certain embodiments of the invention are to be understood as being modified by the term "about."

Artificial Nose Technology

VOC selective detectors or "artificial noses" have developed to detect and characterize gaseous samples. A multitude of technologies have implemented artificial nose functions including, but not limited to: colorimetric sensor arrays, polymer arrays, mass sensitive piezoelectric substrates, surface acoustic wave (SAW) transducers, quartz crystal microbalances, functionalized carbon nanotubes and gold nanoparticles.

Initial work in the field of artificial noses was conducted by Wilkens and Hatman in 1964, though the bulk of research done in this area has been carried out since the early 1980's. See, e.g., W. F. Wilkens, A D. Hatman. Ann. NY Acad. Sci., 116, 608 (1964); K. Pursaud, G. H. Dodd. Nature, 299, 352-355 (1982); and J. W. Gardner, P. N., Bartlett. Sensors and Actuators B, 18-19, 211-220 (1994). Vapor-selective detectors or "artificial noses" are typically based upon the production of an interpretable signal or display upon exposure to a vapor-emitting substance or odorant (hereinafter sometimes referred to as an "analyte"). More specifically, typical artificial noses are based upon selective chemical binding or other molecular interactions in the interface between detecting a compound of the artificial nose and an analyte or odorant, and then transforming that chemical binding into a signal or display, i.e., signal transduction.

Polymer arrays having a single indicator have been used for artificial noses. That is, a series of chemically-diverse polymers or polymer blends are chosen so that their composite response distinguishes a given odorant or analyte from others. Examples of polymer array vapor detectors, including conductive polymer and conductive polymer/carbon black composites, are discussed in: M. S. Freund, N. S. Lewis, Proc. Natl. Acad. Sci. USA 92, 2652-2656 (1995); B. J. Doleman, R. D. Sanner, E. J. Severin, R. H. Grubbs, N. S. Lewis, Anal. Chem. 70, 2560-2564 (1998); T. A Dickinson, J. White, J. S. Kauer, D. R. Walt, Nature 382, 697-700 (1996) (polymer array with optical detection); A E. Hoyt, A J. Ricco, H. C. Yang, R. M. Crooks, J. Am. Chem. Soc. 117, 8672 (1995); and J. W. Grate, M. H. Abraham, Sensors and Actuators B 3, 85-111 (1991).

Other interface materials include functionalized self-assembled monolayers (SAM), metal oxides, and dendrimers. Signal transduction is commonly achieved with mass sensitive piezoelectric substrates, surface acoustic wave (SAW) transducers, or conductive materials. Optical transducers (based on absorbance or luminescence) have also been examined. Examples of metal oxide, SAM, and dendrimer-based detectors are discussed in J. W. Gardner, H. V. Shurmer, P. Corcoran, Sensors and Actuators B 4, 117-121 (1991); J. W. Gardner, H. V. Shurmer, T. T. Tan, Sensors and Actuators B 6, 71-75 (1992); and R. M. Crooks, A. J. Ricco, Acc. Chem. Res. 31, 219-227 (1998). These devices also use a single indicator.

Techniques have also been developed using a metalloporphyrin for optical detection of a specific, single gas such as oxygen or ammonia, and for vapor detection by chemically interactive layers on quartz crystal microbalances. See A. E. Baron, J. D. S. Danielson, M. Gonterman, J. R. Wan, J. B. Callis, Rev. Sci. Instrum. 64, 3394-3402 (1993); J. Kavandi, et al., Rev. Sci. Instrum. 61, 3340-3347 (1990); W. Lee, et al., J. Mater. Chem. 3, 1031-1035 (1993); A. A. Vaughan, M. G. Baron, R. Narayanaswamy, Anal. Comm. 33, 393-396 (1996); J. A. J. Brunink, et al., Anal. Chim. Acta 325, 53-64 (1996); C. DiNatale, et al., Sensors and Actuators B 44, 521-526 (1997); and C. DiNatale, et al., Mat. Sci. Eng. C 5, 209-215 (1998).

Other techniques include functionalized carbon nanotubes sometimes integrated into a transistor, see DNA-Decorated Carbon Nanotubes for Chemical Sensing Cristian Staii and Alan T. Johnson, Jr., Nano Letters 5, 1774-1778 (2005) and functionalized gold nanoparticles see Broza, Y. Y., and Haick, H. Nanomaterial-based sensors for detection of disease by volatile organic compounds. Nanomedicine, 8(5), 785-806 (2013); Barash, O., Peled, N., Hirsch, F. R., and Haick, H. Sniffing the Unique "Odor Print" of Non-Small-Cell Lung Cancer with Gold Nanoparticles. Small, 5(22), 2618-2624 (2009).

Colorimetric Sensor Arrays

Artificial noses based on colorimetric sensor arrays exist that are capable of detecting VOCs at low concentrations and a high degree of accuracy. Colorimetric sensor arrays may detect VOCs by reacting with the compounds and changing color based on the amount and type compounds exposed to the array. The resulting pattern of color changes comprises a high-dimensional fingerprint which enables the identification of complex mixtures, including disease signatures in exhaled breath and in headspace of sealed assays. Various colorimetric sensor arrays are described in the following patent publications to Suslick et al. and all of which are incorporated by reference herein in their entirety: U.S. Pat. No. 6,368,558 to Suslick, U.S. Pat. No. 6,495,102, to Suslick, et al., U.S. Pat. No. 7,261,857, to Suslick et al., and U.S. Patent Publication 2008/0199904.

Chemo-Responsive Indicators

Colorimetric sensor arrays utilizing chemo-responsive (chemically responsive) indicators are capable of detecting individual VOC's and complex VOC mixtures down to low part per billion (ppb) concentrations [10, 11, 25]. "Chemo-responsive indicators" refers to any material that absorbs, reflects, and/or emits light when exposed to electromagnetic radiation, or any other indicator that undergoes a change in spectral properties in response to certain changes in its chemical environment. "Change in spectral properties" generally refers to a change in the frequency and/or intensity of the light the colorant absorbs and/or emits. Chemo-responsive indicators may include dyes and pigments.

For example, the following five classes of chemically-responsive indicators may be utilized: (i) metal-ion-containing indicators that respond to Lewis basicity (i.e., electron pair donation, metal ion ligation), (ii) pH indicators that respond to Brønsted acidity/basicity (i.e., proton acidity and hydrogen bonding), (iii) indicators with large permanent dipoles (e.g., solvatochromic dyes) that respond to molecular polarity, (iv) metal salts that respond to chelation, and (v) redox indicators that monitor redox properties. Utilizing of this broad spectrum of highly sensitive chemical interactions allows a colorimetric sensor array to detect and identify very diverse classes of metabolite compounds.

Porphyrins/Metalloporphyrins

For example, for recognition of analytes with Lewis acid/base capabilities, the use of porphyrins and their metal complexes is desirable. Metalloporphyrins are ideal for the detection of metal-ligating vapors because of their open coordination sites for axial ligation, their large spectroscopic shifts upon ligand binding, their intense coloration, and their ability to provide ligand differentiation based on metal-selective coordination. Furthermore, metalloporphyrins are cross-responsive indicators, showing responses to a large variety of different analytes to different degrees and by different color changes.

Lewis Acid/Base Indicators

A Lewis acid/base indicator is defined as an indicator which has been identified for its ability to interact with analytes by acceptor-donor sharing of a pair of electrons from the analyte. This results in a change in color and/or intensity of color that indicates the presence of the analyte. Lewis acid/base indicators include metal ion-containing or three-coordinate boron-containing indicators. The change in spectral properties for a Lewis acid-base indicator may be related to Lewis acid-base interaction and ligand binding, but also to $\pi$-$\pi$ complexation, hydrogen bonding, and/or polarity changes.

Exemplary Lewis acids include, but are not limited to, metal ion-containing porphyrins (i.e., metalloporphyrins), salen complexes, chlorins, bispocket porphyrins, and phthalocyanines. Diversity within the metalloporphyrins can be obtained by variation of the parent porphyrin, the porphyrin metal center, or the peripheral porphyrin sub stituents. The parent porphyrin is also referred to as a free base porphyrin, which has two central nitrogen atoms protonated (i.e., hydrogen cations bonded to two of the central pyrrole nitrogen atoms). In one example, a parent porphyrin is the so-called free base form 5,10,15,20-tetraphenylporphyrin ($H_2TPP$), its dianion is 5,10,15,20-tetraphenyl-porphyrinate (-2) (TPP dianion), its metalated complexes, and its acid forms ($H_3TPP^+$ and $H_4TPP^{-2}$). This porphyrin may form metalated complexes, for example, with $Sn^{4+}$, $Co^{3+}$, $Co^{2+}$, $Cr^{3+}$, $Mn^{3+}$, $Fe^{3+}$, $Cu^{2+}$, $Ru^{2+}$, $Zn^{2+}$, $Ag^{2+}$, $In^{3+}$, and $Ir^{3+}$.

Metal ion-containing metalloporphyrin indicators are described, for example, in U.S. Pat. No. 6,368,558 to Suslick et al. and in U.S. Patent Application Publication No. 2003/0143112 to Suslick et al., both of which are incorporated by reference herein. Particularly suitable metal ions complexed with indicators for detecting ammonia include Zn(II) and Co(III) metals. In particular embodiments of the present invention, the Lewis acid indicator is a metalloporphyrin. For example, diversity within the metalloporphyrins can be obtained by variation of the parent porphyrin, the porphyrin metal center, or the peripheral porphyrin substituents. The parent porphyrin is also referred to as a free base porphyrin, which has two central nitrogen atoms protonated (i.e., hydrogen cations bonded to two of the central pyrrole nitrogen atoms). A particularly suitable parent porphyrin is 5,10,15,20-tetraphenylporphyrinate(-2) (TPP dianion), its metalated complexes, its so-called free base form ($H_2TPP$) and its acid forms ($H_3TPP^+$ and $H_4TPP^{+2}$). Suitable metal ion-containing metalloporphyrin indicators for use in the apparatus and method of the present invention include, but are not limited to:

2,3,7,8,12,13,17,18-octafluoro-5,10,15,20-tetrakis-(pentafluorophenyl)porphyrinatocobalt(II) [$Co(F_{28}TPP)$];

2,3,7,8,12,13,17,18-octabromo-5,10,15,20-tetraphenylporphyrinatozinc(II) [$Zn(Br_8TPP)$];

5,10,15,20-tetraphenylporphyrinatozinc(II) [ZnTPP];

5(phenyl)-10,15,20-trikis(2',6'-bis(dimethyl-t-butylsiloxyl)phenyl) porphyrinatozinc(II) [Zn(Si6PP)];

5,10,15,20-tetrakis(2',6'-bis(dimethyl-t-butylsiloxyl)phenyl)porphyrinatozinc(II) [Zn (Si8PP];

5,10,15,20-Tetraphenyl-porphyrinatocobalt (II) [CoTPP];

5,10,15,20-Tetrakis(2,6-difluorophenyl)porphyrinatozinc (II) [$ZnF_2PP$]; and 5,10,15,20-Tetrakis(2,4,6-trimethylphenyl)porphyrinatozinc(II) [ZnTMP].

The synthesis of such porphyrins is described in U.S. patent application Ser. No. 10/279,788.

pH Sensitive Indicators

The chemoresponsive indicator may be, for example, a pH sensitive indicator. Indicators that are pH sensitive include pH indicator or acid-base indicator dyes that may change color upon exposure to acids or bases. A Brønsted acid indicator of the present disclosure is a pH indicator dye which changes color in response to changes in the proton (Brønsted) acidity or basicity of the environment. For example, Brønsted acid indicators are, in general, non-metalated indicators that are proton donors which can change color by donating a proton to a Brønsted base (i.e., a proton acceptor). Brønsted acid indicators include, but are not limited to, protonated, but non-metalated, porphyrins, chlorins, bispocket porphyrins, phthalocyanines, and related polypyrrolic indicators. Polypyrrolic indicators, when protonated, are in general pH-sensitive indicators (i.e., pH indicator or acid-base indicator dyes that change color upon exposure to acids or bases).

In one embodiment, a Brønsted acid indicator is a non-metalated porphyrin such as 5,10,15,20-tetrakis(2',6'-bis(dimethyl-t-butylsiloxyl)phenyl)porphyrin dication [$H_4Si_8PP$]$^+_2$; 5,10,15,20-Tetraphenyl-21H,23H-porphine [$H_2TPP$]; or 5,10,15,20-Tetraphenylporphine dication [$H_4TPP$]$^{+2}$. In another embodiment of the instant invention, selected Brønsted acid indicators include, but are not limited to, Bromocresol Purple, Cresol Red, Congo Red, Thymol Blue, Bromocresol Green, Nile Red, Bromothymol Blue, Methyl Red, Nitrazine Yellow, Phenol Red, Bromophenol Red, Disperse Orange 25, and Bromophenol Blue. As will be appreciated by the skilled artisan, the Brønsted acids disclosed herein may also be considered Brønsted bases under particular pH conditions. Likewise, a non-metalated, non-protonated, free base form of a porphyrin may also be considered a Brønsted base. However, these indicator forms are also expressly considered to be within the scope of the indicators disclosed herein.

Examples of Brønsted acid indicators include protonated, but non-metalated, porphyrins; chlorines; bispocket porphyrins; phthalocyanines; and related polypyrrolic indicators. Examples of non-metalated porphyrin Brønsted acid indicators include 5,10,15,20-tetrakis(2',6'-bis(dimethyl-t-butylsiloxyl)phenyl)porphyrin dication; 5,10,15,20-tetraphenyl-21H,23H-porphyrin; or 5,10,15,20-tetraphenylporphyrin dication. Other examples of Brønsted acid indicators include Chlorophenol Red, Bromocresol Green, Bromocresol Purple, Bromothymol Blue, Bromopyrogallol Red, Pyrocatechol Violet, Phenol Red, Thymol Blue, Cresol Red, Alizarin, Mordant Orange, Methyl Orange, Methyl Red, Congo Red, Victoria Blue B, Eosin Blue, Fat Brown B, Benzopurpurin 4B, Phloxine B, Orange G, Metanil Yellow, Naphthol Green B, Methylene Blue, Safranine O, Methylene Violet 3RAX, Sudan Orange G, Morin Hydrate, Neutral Red, Disperse Orange #25, Rosolic Acid, Fat Brown RR, Cyanidin chloride, 3,6-Acridineamine, 6'-Butoxy-2,6-diamino-3,3'-azodipyridine, para-Rosaniline Base, Acridine Orange Base, Crystal Violet, Malachite Green Carbinol Base, Nile Red, Nile Blue, Nitrazine Yellow, Bromophenol Red, Bromophenol Blue, Bromoxylenol Blue, Xylenol Orange Tetrasodium Salt, 1-[4-[[4-(dimethylamino)phenyl]azo]phenyl]-2,2,2-trifluoro-ethanone-, 4-[2-[4-(dimethylamino)phenyl]ethenyl]-2,6-dimethyl-pyrylium perchlorate, and 1-amino-4-(4-decylphenylazo)-naphthalene.

Solvachromatic Dyes

The chemoresponsive dye may be, for example, a solvatochromic dye or a vapochromic dye. Solvatochromic dyes that may be utilized change color in response to changes in the general polarity of their environment, primarily through strong dipole-dipole and dispersion interactions. To some extent, all dyes inherently are solvatochromic, with some being more responsive than others. Particular examples of suitable solvatochromic dyes include, but are not limited to Reichardt's dyes, Nile Red, Disperse Orange #25, Disperse Orange #3, Phenol Blue, Merocyanine 540, 1-Ethyl-4-(2-hydroxystyryl)pyridinium iodide, 4-hydroxystyryl-pyridinium dye, 4-methoxycarbonyl-1-ethylpyridinium iodide, and 2,6-diphenyl-4-(2,4,6-triphenyl-1-pyridinio)-phenolate.

The addition of at least one Brønsted acid dye to an array containing at least one metal ion-containing Lewis acid dye can improve the sensitivity of the array for particular analytes and increase the ability to discriminate between analytes. For example, colorimetric sensor arrays have been shown to detect volatile organic compounds and complex mixtures down to ppb levels (Rakow, et al. (2005) Angew. Chem. Int. Ed. 44:4528-4532). Further, the use of one or more metal ion-containing dyes in combination with one or more Brønsted acid dyes can advantageously create a signature indicative of the presence of a particular analyte. Thus, while some embodiments may utilize at least one Lewis acid and/or base dye, one Brønsted acidic and/or basic dye, or one zwitterionic solvatochromic dye, other embodiments of this disclosure may utilize use at least two different classes of dyes on the instant arrays. In one embodiment, the colorimetric sensor array contains at least one Lewis acid and/or base dye, one Brønsted acidic and/or basic dye, or one zwitterionic solvatochromic dye. In another embodiment, the colorimetric sensor array contains at least one Lewis acid and/or base dye and one Brønsted acidic and/or basic dye. In a further embodiment, the colorimetric sensor array contains at least one Lewis acid and/or base dye and one zwitterionic solvatochromic dye. In yet a further embodiment, the colorimetric sensor array contains at least one Brønsted acidic and/or basic dye and one zwitterionic solvatochromic dye. Still further embodiments may utilize at least three different classes of dyes on the instant arrays, i.e., at least one Lewis acid and/or base dye, one Brønsted acidic and/or basic dye, and one zwitterionic solvatochromic dye.

An array that includes a pH sensitive dye and/or a solvatochromic or vapochromic dye may be useful in differentiating analytes that do not bind to, or bind only weakly to, metal ions. Such analytes include acidic compounds, such as carboxylic acids, and certain organic compounds lacking ligatable functionality. Examples of organic compounds lacking ligatable functionality include simple alkanes, arenes, and some alkenes and alkynes, especially if sterically hindered. Examples of organic compounds lacking ligatable functionality also include molecules that are sufficiently sterically hindered to preclude effective ligation. Arrays that include a pH sensitive and/or a solvatochromic or vapochromic dye are described, for example, in U.S. Patent Application Publication No. 2003/0143112 to Suslick et al., which is incorporated by reference herein.

Redox Sensitive Indicators

The chemoresponsive indicator may be, for example, a redox sensitive indicator that undergoes a change in spectral properties depending upon its oxidation state. Examples of dyes that are redox sensitive include redox indicators such as methylene blue, naphthol blue-black, brilliant ponceau, alpha-naphthoflavone, basic fuchsin, quinoline yellow, thionin acetate, methyl orange, neutral red, diphenylamine, diphenylaminesulfonic acid, 1,10-phenanthroline iron(II), permanganate salts, silver salts, and mercuric salts.

Metal Ion Sensitive Indicators

The chemoresponsive indicator may be, for example, a metal ion sensitive indicator that undergoes a change in spectral properties in the presence of metal ions. Examples of dyes that are metal ion sensitive include metal ion indicators, such as eriochrome black T, murexide, 1-(2-pyridylazo)-2naphthol, and pyrocatechol violet.

Deficiencies of Existing Arrays

As disclosed herein, existing arrays do not contain sufficient indicators for detecting electrophilic analytes. For instance, while a single nucleophilic indicator has been used in an array, that alone has not produced an array sensitive enough to detect electrophilic analytes. Particularly, prior arrays did not detect certain aldehydes, esters and ketones with a high degree of accuracy or sensitivity.

This is particularly relevant because aldehydes and ketones are useful analytes to detect a variety of cancers. Additionally, formaldehyde detection is useful because formaldehyde is a frequent pollutant. Also, organophosphates (esters) are electrophilic compounds used in pesticides and chemical warfare agents. Accordingly, the use of compounds that can detect electrophilic compounds with a high degree of sensitivity and selectivity would be highly useful.

However, previous efforts have failed to produce an array that could detect electrophilic compounds with a high degree of sensitivity and accuracy. For instance, in some cases, nucleophilic amines (a nucleophilic agent) have been used with a pH indicator. Therefore, reactions of nucleophilic agents with electrophilic analytes would result in the change in acidity that can be detected with a pH indicator. However, in those cases the pH indicator would be highly cross-reactive toward acidic analytes, and could not readily discriminate between acidic and electrophilic analytes. These nucleophilic agents were not sensitive enough primarily because the nucleophilic agent did not contain a chromophore. The chemistry involved only a rough indication of pH changes with a secondary pH indicator molecule.

In a few prior examples, a single nucleophilic indicator (nucleophilic molecule that includes a chromophore as defined herein) has been used in an array. However, in those cases, the sensitivity and selectivity was not satisfactory to be practically useful because the array only contained a single nucleophilic indicator.

Arrays with Nucleophilic Indicators

Accordingly, it was investigated as to whether an array of at least two or more nucleophilic indicators could be sufficiently sensitive to both detect and discriminate different kinds of electrophilic analytes better than existing nucleophilic agents. Accordingly, it was discovered that an array of nucleophilic indicators had a surprising sensitivity and selectivity to identify and classify nucleophilic compounds at very low concentrations. For instance, it was discovered that formaldehyde could be detect at 10 ppb using an array of nucleophilic indicators.

Additionally, it was determined that a nucleophilic array could detect volatile electrophilic biomarkers for colon cancer in exhaled breath, and organophosphates in liquid form. Accordingly, it was discovered that using a multitude of nucleophilic indicators has the sensitivity to more accurately detect electrophilic molecules.

The nucleophilic indicators used for these investigations were defined herein as "nucleophilic indicators." These are defined herein as nucleophilic molecules that include a chromophore. Accordingly, the indicator itself changes color. This is opposed to a nucleophilic agent—a molecule without a chromophore—that undergoes a chemical change that is detected by a secondary indicator molecule. For instance, some nucleophilic agents exhibit a change in pH when interacting with electronic rich molecules, and therefore the nucleophilic agent in combination with a pH indicator can detect electrophilic analytes. However, it has been discovered that an array of nucleophilic indicators, which has a chromophore attached to the nucleophilic molecule itself, is much more sensitive and selective than a nucleophilic agent.

Chemoresponsive Pigments

The chemoresponsive indicator may be a chemoresponsive pigment. In some cases, the chemoresponsive pigment is a porous pigment in which chemoresponsive dyes are immobilized in a porous matrix. A porous pigment particle has a chemoresponsive surface area that is much greater than the chemoresponsive surface area of a corresponding non-porous pigment particle. Examples of porous matrices include porous calcium carbonate, porous magnesium carbonate, porous silica, porous alumina, porous titania, and zeolites.

Chemoresponsive Nanoparticle

The chemoresponsive indicator may be a chemoresponsive nanoparticle. A chemoresponsive nanoparticle may be a discrete nanoparticle, or it may be formed from nanoparticle-forming ions or molecules. The nanoparticle may be in a variety of forms, including a nanosphere, a nanorod, a nanofiber, and a nanotube. Examples of chemoresponsive nanoparticles include nanoporous porphyrin solids, semiconductor nanoparticles such as quantum dots, and metal nanoparticles.

Array of Indicators

The use of more than one type of chemoresponsive colorant may expand the range of analytes to which the array is sensitive, may improve sensitivity to some analytes, and/or may increase the ability to discriminate between analytes. In some cases, a colorimetric array includes 2 to 1,000 sensors, 4 to 500 sensors, or 8 to 250 sensors. In certain cases, a colorimetric array includes from 10 to 100 sensors (e.g., 16 to 80 sensors, 36 sensors, or 60 sensors). Each sensor in a colorimetric array may include a different colorant. However, it may be desirable to include duplicate sensors that include the same colorant. Duplicate sensors may be useful, for example, to provide redundancy to the array and/or to serve as an indicator for quality control. Table 1 lists exemplary chemoresponsive indicators for a colorimetric sensor array having 36 sensors.

TABLE 1

Exemplary chemoresponsive colorants for a colorimetric sensor array.

| No. | Colorant |
|---|---|
| 1 | 5,10,15,20-Tetraphenyl-21H,23H-porphine zinc (II) |
| 2 | 5,10,15,20-Tetraphenyl-21H,23H-porphine copper (II) |
| 3 | 5,10,15,20-Tetraphenyl-21H,23H-porphine manganese (III) chloride |
| 4 | 2,3,7,8,12,13,17,18-Octaethyl-21H,23H-porphine iron (III) chloride |
| 5 | 5,10,15,20-Tetraphenyl-21H,23H-porphine cobalt (II) |
| 6 | meso-Tetra(2,4,6-trimethylphenyl)porphine |
| 7 | Nitrazine Yellow (basic) |
| 8 | Methyl Red (basic) |
| 9 | Chlorophenol Red (basic) |
| 10 | Napthyl Blue Black |
| 11 | Bromothymol Blue (basic) |
| 12 | Thymol Blue (basic) |
| 13 | m-Cresol Purple (basic) |
| 14 | Zinc (II) acetate with m-Cresol purple (basic) |
| 15 | Mercury (II) chloride with Bromophenol Blue (basic) |
| 16 | Mercury (II) chloride with Bromocresol Green (basic) |
| 17 | Lead (II) acetate |
| 18 | Tetraiodophenolsulfonephthalein |
| 19 | Fluorescein |
| 20 | Bromocresol Green |
| 21 | Methyl Red |
| 22 | Bromocresol Purple |
| 23 | Bromophenol Red |
| 24 | Brilliant Yellow |
| 25 | Silver nitrate + Bromophenol Blue (basic) |
| 26 | Silver nitrate + Bromocresol Green (basic) |
| 27 | Cresol Red (acidic) |
| 28 | Disperse Orange 25 |
| 29 | m-Cresol Purple |
| 30 | Nitrazine Yellow |
| 31 | Cresol Red |
| 32 | Bromocresol Green |
| 33 | Phenol Red |
| 34 | Thymol Blue |
| 35 | Bromophenol Blue |
| 36 | m-Cresol Purple |

Table 2 lists example of an array that incorporate nucleophilic indicators for a vapor sensor.

TABLE 2

Exemplary chemoresponsive colorants for a colorimetric sensor array incorporating nucleophilic indicators for a vapor sensor:

| No. | Colorant |
|---|---|
| 1 | Purpald + TBAOH |
| 2 | Purpald + TBAOH |
| 3 | Fiducial (carbon black) |
| 4 | Parosoaniline |
| 5 | Parosoaniline |
| 6 | Acetylacetone + 2,3,4,5,6-pentafluorobenzylhydroxylamine hydrochloride |
| 7 | Acetylacetone + 2,3,4,5,6-pentafluorobenzylhydroxylamine hydrochloride |
| 8 | Acetylacetone + 2,3,4,5,6-pentafluorobenzylhydroxylamine hydrochloride |
| 9 | Acetylacetone + 5-aminofluorescein |
| 10 | Acetylacetone + 5-aminofluorescein |
| 11 | Acetylacetone + 5-Aminofluorescein |
| 12 | 2 4-Dinitrophenylhydrazine + TsOH |
| 13 | 2 4-Dinitrophenylhydrazine |
| 14 | 2 4-Dinitrophenylhydrazine |
| 15 | 2 4-Dinitrophenylhydrazine + 4-Nitroaniline |
| 16 | 2 4-Dinitrophenylhydrazine + 4-Nitroaniline |
| 17 | 2 4-Dinitrophenylhydrazine + 4-Nitroaniline |
| 18 | 3-Methyl-2-benzothiazolinone hydrazine + Fe(NO$_3$)$_3$ |
| 19 | 3-Methyl-2-benzothiazolinone hydrazine + Fe(NO$_3$)$_3$ |
| 20 | 3-Methyl-2-benzothiazolinone hydrazine + Pb(OAc)$_4$ |
| 21 | 3-Methyl-2-benzothiazolinone hydrazine + Pb(OAc)$_4$ |
| 22 | Chromotropic acid + Ag$_2$O |

TABLE 2-continued

Exemplary chemoresponsive colorants for a colorimetric sensor array incorporating nucleophilic indicators for a vapor sensor:

| No. | Colorant |
|---|---|
| 23 | Chromotropic acid + $Ag_2O$ |
| 24 | Chromotropic acid + $Ag_2O$ |
| 25 | N-(Rhodamine B)-deoxylactam-ethylenediamine + TBAOH |
| 26 | N-(Rhodamine B)-deoxylactam-ethylenediamine + TBAOH |
| 27 | N-(Rhodamine B)-deoxylactam-ethylenediamine + TBAOH |
| 28 | [4-[(3,5-Dimethyl-1H-pyrrol-2-yl-N)(3,5-dimethyl-2H-pyrrol-2-ylidene-N)methyl]-1,2-benzenediaminato]difluoroboron |
| 29 | [4-[(3,5-Dimethyl-1H-pyrrol-2-yl-N)(3,5-dimethyl-2H-pyrrol-2-ylidene-N)methyl]-1,2-benzenediaminato]difluoroboron + $Sc(OTf)_3$ |
| 30 | 5-Aminofluorescein |
| 31 | 4,4-Dimethylaminostyryl pyridine |
| 32 | 4,4-Dimethylaminostyryl pyridine |

Table 3 lists example of an array that incorporate nucleophilic indicators for a liquid sensor.

TABLE 3

Exemplary chemoresponsive colorants for a colorimetric sensor array incorporating nucleophilic indicators for a liquid sensor:

| No. | Colorant |
|---|---|
| 1 | Ethyl bis(2,4-dinitrophenyl) acetate |
| 2 | Yellow dye A2 |
| 3 | Red dye E |
| 4 | Nitrazine Yellow |
| 5 | Methyl Red + TBAOH |
| 6 | Tetraiodophenolsulfonephthalein |
| 7 | Bromocresol Green |
| 8 | [4-[3,5-dimethyl-1H-pyrrol-2-yl-N)(3,5-dimethyl-2H-pyrrol-2-ylidene-N)methyl]-1,2-benzenediaminato]difluoroboron + NaOH |
| 9 | Fiducial (carbon black) |
| 10 | (E)-5,5-Difluoro-7-(4-([2-(2-hydroxyethoxy)ethyl]-(methyl)amino)styrl)-1,3,9-trimethyl-10-phenyl-5H-dipyrrolo(1,2-c:2',1'-f](1,3,2)diazaborinin-4-ium-5-uide – Europium(III) complex + NaOH |
| 11 | (E)-5,5-Difluoro-7-(4-([2-(2-hydroxyethoxy)ethyl]-(methyl)amino)styrl)-1,3,9-trimethyl-10-phenyl-5H-dipyrrolo(1,2-c:2',1'-f](1,3,2)diazaborinin-4-ium-5-uide + NaOH |
| 12 | Co(II)TPP + Bromocresol purple |
| 13 | Zn(II)TPP + Bromophenol blue |
| 14 | Pyrocatechol violet + TBAOH |
| 15 | 2,6-dichloroindophenol sodium salt hydrate + TBAOH |
| 16 | $Sn(IV)TPPCl_2$ |
| 17 | Fiducial (carbon black) |
| 18 | $HgCl_2$ + Bromocresol Green + TBAOH |
| 19 | $LiNO_3$ + Cresol Red + TBAOH |
| 20 | 5-Aminofluorescein |
| 21 | Co(II)TPP |
| 22 | N-(rhodamine B)-deoxylactam-ethylenediamine + TBAOH |
| 23 | Mg(II)TPP |
| 24 | 1-Methyl-2-phenylidone |
| 25 | Fiducial (carbon black) |
| 26 | Mn(III)TPPCl |
| 27 | Fe(III)OEPCl |
| 28 | Rh(III)TPPCl |
| 29 | Zn(II)TMP |
| 30 | 4-Aminophenyl sulfone |
| 31 | Copper (II) neodecanoate |
| 32 | 4-(4-Nitrobenzyl)pyridine + N-Benzylaniline |

Table 4 lists example of an array that incorporate nucleophilic indicator indicators for a vapor sensor.

TABLE 4

Exemplary chemoresponsive colorants for a colorimetric sensor array incorporating nucleophilic indicators for a vapor sensor:

| No. | Colorant |
|---|---|
| 1 | Ethyl bis(2,4-dinitrophenyl) acetate |
| 2 | Yellow dye A2 |
| 3 | Red dye E |
| 4 | Nitrazine Yellow |
| 5 | Methyl Red + TBAOH |
| 6 | Tetraiodophenolsulfonephthalein |
| 7 | Bromocresol Green |
| 8 | [4-[3,5-dimethyl-1H-pyrrol-2-yl-N)(3,5-dimethyl-2H-pyrrol-2-ylidene-N)methyl]-1,2-benzenediaminato]difluoroboron + NaOH |
| 9 | Fiducial (carbon black) |
| 10 | (E)-5,5-Difluoro-7-(4-([2-(2-hydroxyethoxy)ethyl]-(methyl)amino)styrl)-1,3,9-trimethyl-10-phenyl-5H-dipyrrolo(1,2-c:2',1'-f](1,3,2)diazaborinin-4-ium-5-uide – Europium(III) complex + NaOH |
| 11 | (E)-5,5-Difluoro-7-(4-([2-(2-hydroxyethoxy)ethyl]-(methyl)amino)styrl)-1,3,9-trimethyl-10-phenyl-5H-dipyrrolo(1,2-c:2',1'-f](1,3,2)diazaborinin-4-ium-5-uide + NaOH |
| 12 | Co(II)TPP + Bromocresol purple |
| 13 | Zn(II)TPP + Bromophenol blue |
| 14 | Pyrocatechol Violet + TBAOH |
| 15 | 2,6-Dichloroindophenol sodium salt hydrate + TBAOH |
| 16 | $Sn(IV)TPPCl_2$ |
| 17 | Fiducial (carbon black) |
| 18 | $HgCl_2$ + Bromocresol Green + TBAOH |
| 19 | $LiNO_3$ + Cresol Red + TBAOH |
| 20 | 5-Aminofluorescein |
| 21 | Co(II)TPP |
| 22 | N-(rhodamine B)-deoxylactam-ethylenediamine + TBAOH |
| 23 | Mg(II)TPP |
| 24 | 1-Methyl-2-phenylidone |
| 25 | Fiducial (carbon black) |
| 26 | Mn(III)TPPCl |
| 27 | Fe(III)OEPCl |
| 28 | Rh(III)TPPCl |
| 29 | Zn(II)TMP |
| 30 | 4-Aminophenylsulfone |
| 31 | Copper (II) neodecanoate |
| 32 | 4-(4-Nitrobenzyl)pyridine + N-Benzylaniline |

Indicator Formulation

Indicators may be made with any number of formulations. For instances, some indicators may be made in plasticizer formulations. These formulations are generally liquids and may spread out quite a bit over time. In other examples, formulations include polymer based formations that form a polymeric network to deposit the indicator. For instance, polymer based formulations may include, cellulous, polystyrene, polyvinyl alcohol, poly(methyl methacrylate) or polyvinyl chloride. In other examples, nanoporous material may be used to form nanoporous pigments. Certain host materials may be more suitable for certain analytes and/or indicators, depending on affinity, surface area, and interactions with the indicator or analyte.

The nanoporous material may be used to convert a dye to a nanoporous pigment. The nanoporous pigment may be made from a nanoporous material and a first immobilized, chemoresponsive colorant. In some examples, an array will be formed by depositing a first liquid that is a nanoporous material precursor and a chemoresponsive colorant that may be a prepolymer, ceramic precursor or mixtures of these. Then, the nanoporous precursor may be solidified to form a nanoporous material. The first nanoporous material precursor may be, for example, a polymer, a prepolymer, ceramic precursors, or mixtures of these. The first liquid may include other ingredients, such as a solvent and/or a surfactant.

The first nanoporous material precursor may include starting materials for a ceramic that have been at least partially hydrolyzed. The first liquid may be formed by combining ingredients including starting materials for a ceramic, a solvent, and the first chemoresponsive colorant to form a first mixture, and then hydrolyzing the first mixture to form a sol. Solidifying the first nanoporous material precursor may include condensing the first nanoporous material precursor to form a gel, and drying the gel to form the first nanoporous material.

The solidifying may include any method that converts the nanoporous material precursor into a nanoporous material. Examples of solidification methods include chemical cross-linking, exposure to UV radiation, and heating. In one example, the solidifying includes heating the liquid on the substrate. Initial curing at room temperature for 24 to 72 hours may be preferred in order to maintain porosity of the nanoporous pigment. Additional heating may be performed, for example, in a standard convection oven. If the substrate is temperature-sensitive, heating the liquid for 24 hours at temperatures lower than 70° C. is preferred. When preparing a spot that includes a nanoporous ceramic and a pH responsive indicator as the chemoresponsive colorant, solidifying at 60° C. or even at room temperature is preferred. With more thermally robust substrates, solidifying may be completed much more rapidly, for example in 1 hour at 120° C.

The nanoporous material may be any material that includes pores, reticulations or void spaces with dimensions from 0.2 to 1000 nm. Preferably the nanoporous material includes pores with dimensions from 0.5 to 100 nm. Preferably the nanoporous material includes pores that are interconnected, such that a fluid can flow between the pores of the material. A nanoporous material may be, for example, an inorganic network, such as a porous ceramic or a zeolite. A nanoporous material may be, for example, an organic network, such as a collection of carbon tubes or a cross-linked gel. A nanoporous material may be, for example, a membrane material, such as a microfiltration membrane or an ultrafiltration membrane. A nanoporous material may be a combination of an inorganic network, an organic network and/or a membrane, such as an inorganic/organic composite.

A nanoporous pigment may be fabricated by the immobilization of chemically responsive dyes in organically modified siloxanes (ormosils). In some embodiments, the pigment is created by utilizing an electronic spray to generate an aerosol from precursor solutions containing the dye and other materials, which is then heated to form dye encapsulated microspheres. These dye-encapsulated microspheres can then be printed on paper, such as chromatography paper to form a colorimetric sensor array. These porous sol-gel ormosils may provide a good matrix for colorants due to high surface area, good stability over a wide range of pH, relative inertness in many environments, and transparency in the UV-visible spectrum.

A nanoporous sol-gel matrix has enormous surface area at a microscopic scale, which results in the part-per-billion (ppb) sensitivity. In some embodiments, a nanoporous sol-gel matrix may be required to detect the trace volatile organic compound (VOC) signatures of lung cancer and other diseases in urine or other biological fluids. The nanoporous pigment is a silicon-based sol-gel with enormous surface area, vastly increasing interaction opportunities between analyte and indicator and thereby achieving great sensitivity across a wide range of volatile molecules, including species crucial for cancer diagnosis. Furthermore, the high chemical resistance of the nanoporous pigment allows a manufacturer to increase the chemical diversity of the dyes deposited on the nanoporous substrate by adding chromogenic reagents that were too reactive to incorporate onto substrates comprised of different materials. Nanoporous pigments are more fully described in Lim et al., Chemically Responsive Nanoporous Pigments: Colorimetric Sensor Arras and the Identification of Aliphatic Amines, Langmuir 24 (22), 2008, which is incorporated by reference herein in its entirety.

Indicator Formulations—Nucleophilic Indicators

The indicator performance can be substantially influenced by the selection of host materials. For sensing application, the indicator must be immobilized in a host material, but accessible to the analyte. The nonreactive host material must be able to retain the indicator in place to prevent dye leaching or spreading over time, but porous enough to allow free diffusion of the analyte to the indicator. Furthermore, the indicator needs to be solvated to interact with analytes. When an indicator crystallizes in the host material, the reactivity of the indicator may diminish and only the surface of the crystal will react. Hence, custom formulations suited for different nucleophilic indicators are developed, which include polymer based formulations, sol-gel (e.g. nanoporous) formulations, and plasticizer based formulations. Accordingly, each formulation may be customized based on the indicator or the substrate.

Indicator Substrate

In accordance with the present invention, the plurality of chemo-responsive indicators may be deposited on an array substrate in a predetermined pattern combination. Alternatively stated, the indicators are arranged in a two-dimensional (or linear or other arrangement) spatially-resolved configuration so that upon interaction with one or more analytes, a distinct color and intensity response of each indicator creates a signature indicative of the one or more analytes. A plurality of chemoresponsive indicators encompasses 2, 3, 4, 5, 6, 7, 8, 9, 10, 15, 20, 25, 30, 35, 40, or 50 individual indicators. In particular embodiments, a plurality of chemo-responsive indicators is 2 or more, 5 or more, 10 or more, 15 or more, 20 or more, 25 or more, or 30 or more indicators. The chemo-responsive indicators can be deposited in predetermined pattern combinations of rows, columns, spirals, etc., and one or more chemoresponsive indicator arrays can be used in a container. Indicators can be covalently or non-covalently affixed in or on a colorimetric sensor array substrate by direct deposition, including, but not limited to, pin-printing, airbrushing, ink-jet printing, screen printing, stamping, micropipette spotting, or nanoliter dispensing.

The substrate for retaining the chemo-responsive indicators may be any suitable material or materials, including but not limited to, chromatography plates, paper, filter papers, porous membranes, or properly machined polymers, glasses, or metals. In some embodiments, the substrate may be a hydrophobic or hydrophilic substrate.

Exposure of the Array to Analytes

For gas or vapor analytes, a gas stream containing the analyte is passed over the array, and images may be obtained before, during and/or after exposure to the gas stream. Preferably, an image is obtained after the sample and the array have equilibrated. If the gas stream is not pressurized, it may be useful to use a miniaturized pump or fan.

For analytes dissolved in a solvent, either aqueous or non-aqueous, the first image may be obtained in air or, preferably, after exposure to the pure carrier solvent that is used of the sample. The second image of the array may be obtained after the start of the exposure of the array to the sample. Preferably an image is obtained after the sample and the array have equilibrated.

A colorimetric sensor array may be used to detect analytes in exhaled breath. Detection of compounds in exhaled breath can be useful in detecting infection or disease. The colorimetric detection of ammonia in exhaled breath is described, for example, in U.S. Patent Application Publication No. 2005/0171449 to Suslick et al., which is incorporated by reference herein.

The colorimetric sensor array may be in gaseous or liquid communication with a fluidic sample and/or a solid or liquid culture medium, or other materials containing the sample. This will allow volatile organic compounds (VOCs) emitted from the sample (e.g. from microorganisms in the sample) to evaporate into the headspace of the container and come into contact with the colorimetric sensor array. In other examples, analytes will be contained in the liquid and will react with the colorimetric sensor once they contact the sensor array. In some embodiments, the container is sealed, and the colorimetric sensor array is exposed to VOCs emitted from the microorganisms or other sources of VOCs. In other embodiments, different containers or other mechanisms could be utilized to expose the colorimetric sensor array to gas emitted from the sample. This could include various channels or tubing that could transport the volatile organic compounds emitted from the sample into a gaseous state.

Analyte Detection—Nucleophilic Indicators

Nucleophilic indicators are particularly suited to detecting electron deficient molecules or electrophilic analytes. For instance, certain types of aldehydes, ketones, and esters are particularly well detected by nucleophilic indicators.

Aldehydes are important for a variety of reasons, including for the detection of formaldehyde. Formaldehyde occurs in the environment up to 0.03 ppm parts of air. Materials that incorporate formaldehyde, such as formaldehyde foam insulation (UFFI), can release it in the form of gas or vapor. For instance, pressed-wood products are a major source of formaldehyde indoor pollution. Cigarette smoke, gas stoves, wood-burning stoves, and kerosene heaters can also release formaldehyde. It is toxic to both plants and animals, and is particularly dangerous for the human eyes.

Formaldehyde pollution can also be found in water, and originates from oxidation of organic matter during ozonation and chlorination. In drinking water, it can arise from leaching from plastic fittings and water treatment processes.

Accordingly, detection of formaldehyde in gaseous and liquid states is quite important for detection of pollution. However, obtaining a practical method that is sensitive enough can be difficult. See, e.g. Dai, et al. "A simple spot test quantification method to determine formaldehyde in aqueous samples." Accordingly, the disclosed arrays with nucleophilic indicators provide a much more sensitive and selective method to detect formaldehyde.

Aldehydes (and ketones) are also important class of biomarkers in breath analysis, including cancer diagnosis. A plethora of aldehydes and ketones have been linked to various cancers. However, these biomarkers may be trace amounts in bodily fluids or exhaled gasses and mixed with a plethora of different signals. Accordingly, developing a test sensitive enough to detect cancer in a patient requires extraordinary sensitivity and selectivity. As disclosed below, a breath test to detect biomarkers for cancer using a nucleophilic sensor array has been developed. Table 5 illustrates examples of cancer biomarkers that may be detected using nucleophilic indicators.

TABLE 5

Exemplary disease biomarkers that react with nucleophilic indicators:

| Analyte | Chemical Class | Disease Biomarker |
|---|---|---|
| 1-phenyl-ethanone | ketones | Breast cancer |
| 2,3-dihydro-1-phenyl-4(1H)-quinazolinone | ketones | Breast cancer |
| 2-butanone | ketones | Lung cancer, chronic liver disease |
| 2-pentanone | ketones | Lung cancer, chronic liver disease |
| 3-hydroxy-2-butanone | ketones | Lung cancer |
| acetone | ketones | Lung cancer, diabetes/hyperglycemia, chronic liver disease, stomach cancer, gastro-esophageal cancer, homeostatic balance control |
| 2-methylbutanal | aldehydes | Emphysema |
| acetaldehyde | aldehydes | Alcoholism, gastro-esophageal cancer, liver disease |
| butanal | aldehydes | Lung cancer |
| formaldehyde | aldehydes | Lung cancer, breast cancer, gastro-esophageal cancer |
| furfural | aldehydes | Gastric ulcer |
| heptanal | aldehydes | Lung cancer, breast cancer |
| hexanal | aldehydes | Lung cancer |
| nonanal | aldehydes | Lung cancer |
| pentanal | aldehydes | Lung cancer |
| propanal | aldehydes | Lung cancer |

Additionally, nucleophilic indicators may be useful for detection of organophosphates. These analytes are used in pesticides and insecticide; therefore, the arrays may be useful for detection of pollution. In other examples, organophosphates may be utilized for nerve gas or other chemical weapons. Accordingly, testing for organophosphates may have some particularly useful military applications.

Detection of Artificial Nose Response

Detector

In embodiments where a colorimetric sensor array is utilized as the artificial nose technology, the color changes of the chemically responsive indicators may be detected by any suitable optical or other detector. In embodiments pertaining to a colorimetric sensor array, a detector may monitor the spectroscopic response, transmission response or reflectance response of the indicators on the colorimetric sensing element at one or more wavelengths in a spatially resolved fashion so that all of the spots in the colorimetric sensor array are individually imaged or addressed and the color of each spot is individually determined. For the purposes of the present disclosure, the terms color and colorimetric are intended to include wavelengths in the visible portion of the electromagnetic spectrum, as well as the invisible portion of the electromagnetic spectrum, e.g., infrared and ultraviolet.

Color detection can be accomplished with an imaging spectrophotometer, a flatbed scanner, slide scanner, a video or CCD or CMOS digital camera, or a light source combined with a CCD or CMOS detector. Any still or video as well as analog or digital camera can be employed. Moreover, any imaging format can be used, e.g., RGB (red, green and blue) or YUV. Even simple gray scale imaging can be used. In other embodiments utilizing other artificial nose technologies, a detector or sensor may similarly be used to provide a response of the detector indicative of the molecular interactions occurring at the detector probe or other sensor.

The sensitivity of a colorimetric sensor array is primarily a function of two factors, the ability of an indicator spot to change color when exposed to an analyte and the ability of the detector to measure that color change.

In some embodiments, an optical spectroscopic measurement system can divide the visible spectrum into as many as individual bandpass windows whereas a three-color imaging system by definition contains only three such windows. An optical spectroscopic measurement system is therefore capable of detecting smaller color changes than can be detected by three-color imaging systems, effectively increasing the sensitivity of the entire cross-responsive sensing system. Accordingly, in particular embodiments of the present disclosure, an optical spectroscopic measurement system is employed as a detector. As used herein, optical spectroscopic measurement systems refer to any system that yields higher color resolution than a three-color imaging system. This can be an imaging spectrograph, fiber optic probe(s) coupled to a spectrograph, or other spectroscopic system.

Detectors for Arrays with Nucleophilic Indicators

In some examples, it was determined that a detector capable of sensing ultraviolet ("UV") rays recorded optimal difference in detecting certain types of analytes using nucleophilic indicators. For instance, differences in colorimetric response could not be reliably detected in the RGB range, and instead were only recorded in the UV range. Accordingly, in some examples, a nucleophilic detector and analysis will be performed in the UV range to find optimal differences.

Detection Process and System Setup

Figure 2:
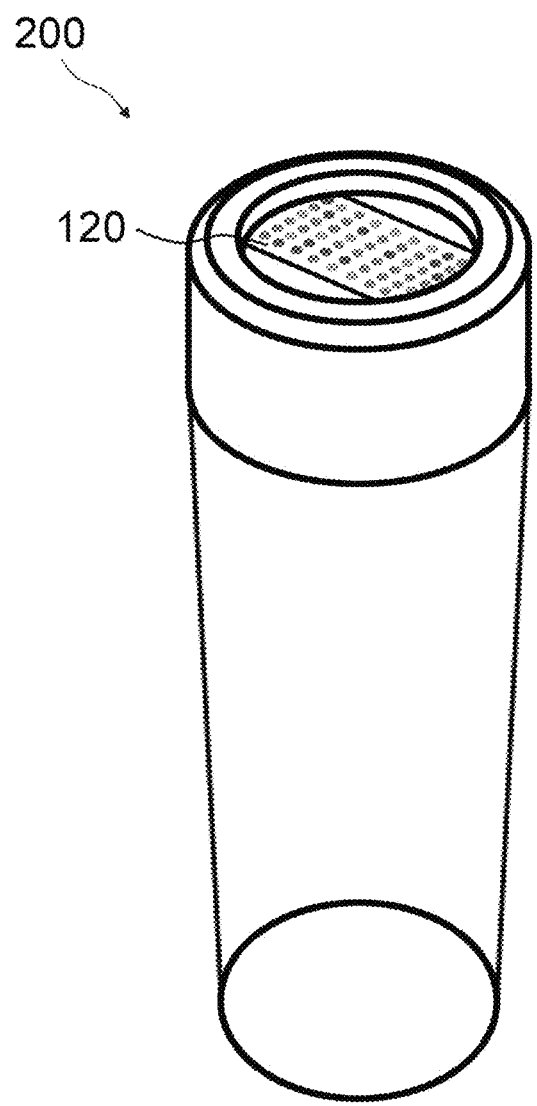
FIG. 2 depicts a perspective view of an example container and sensor array.

FIG. 1 illustrates an example of a system, in some embodiments, where the sample and container 200, as shown in FIG. 2, are maintained at a constant temperature by an incubator. Referring back to FIG. 1, in some embodiments, the detector 130 may be incorporated into an incubator to allow the detector 130 to continuously, or intermittently record the colorimetric response of the indicators 710 through a window 270 while leaving the sample undisturbed at constant temperature. After application of the VOCs contained in the urine may begin to react with the colorimetric sensor array 120.

Prior to application of a sample, a detector 130 may record an image of the presently loaded sensor array 120 as a control for later comparison and subtraction of color changes. Accordingly, this will allow the system to measure color changes based on variation from that particular array's initial color profile. In embodiments associated with other artificial nose technologies, the detector may record an initial reading for comparison to a later reading after introduction of a sample. After application of a sample to a sensor container 200, a detector 130 may at various intervals or after a set time interval, detect and record the colorimetric response of the indicators 710 or other detector 130 response. In some embodiments, software may be configured on server 150 or processing device 140 for automatically controlling the precise timing of detector 130 and recording of the data captured by detector 130. For example, the detector 130 may record an image every minute, every 2, 3, 4, 5, 6, 7, 8, 9 or 10 minutes, or at intervals in-between, or at 20 or 30 minutes, or other suitable intervals. In some embodiments, the detector 130 may continuously record data from the colorimetric sensor array 120. The detector 130 may record images for an hour, 2, 3, 4, 5, 6, hours, or other suitable time frame. In some embodiments, the time frame may be selected based on when the color change rate is near homeostasis or has stopped reacting. In other embodiments, the color change may be stopped when a color change rate drops below a certain threshold.

FIG. 2 depicts exemplary container 200 with colorimetric sensor array 120 for detecting volatile organic compounds emitted from a sample. Container 200 may include a solid or liquid culture medium generally known in the art. A sample, such as a fluid sample (e.g., blood, sputum, exhaled breath) from a mammal, a tissue sample from a mammal, or the like, is placed or injected in container 200.

Figure 3:
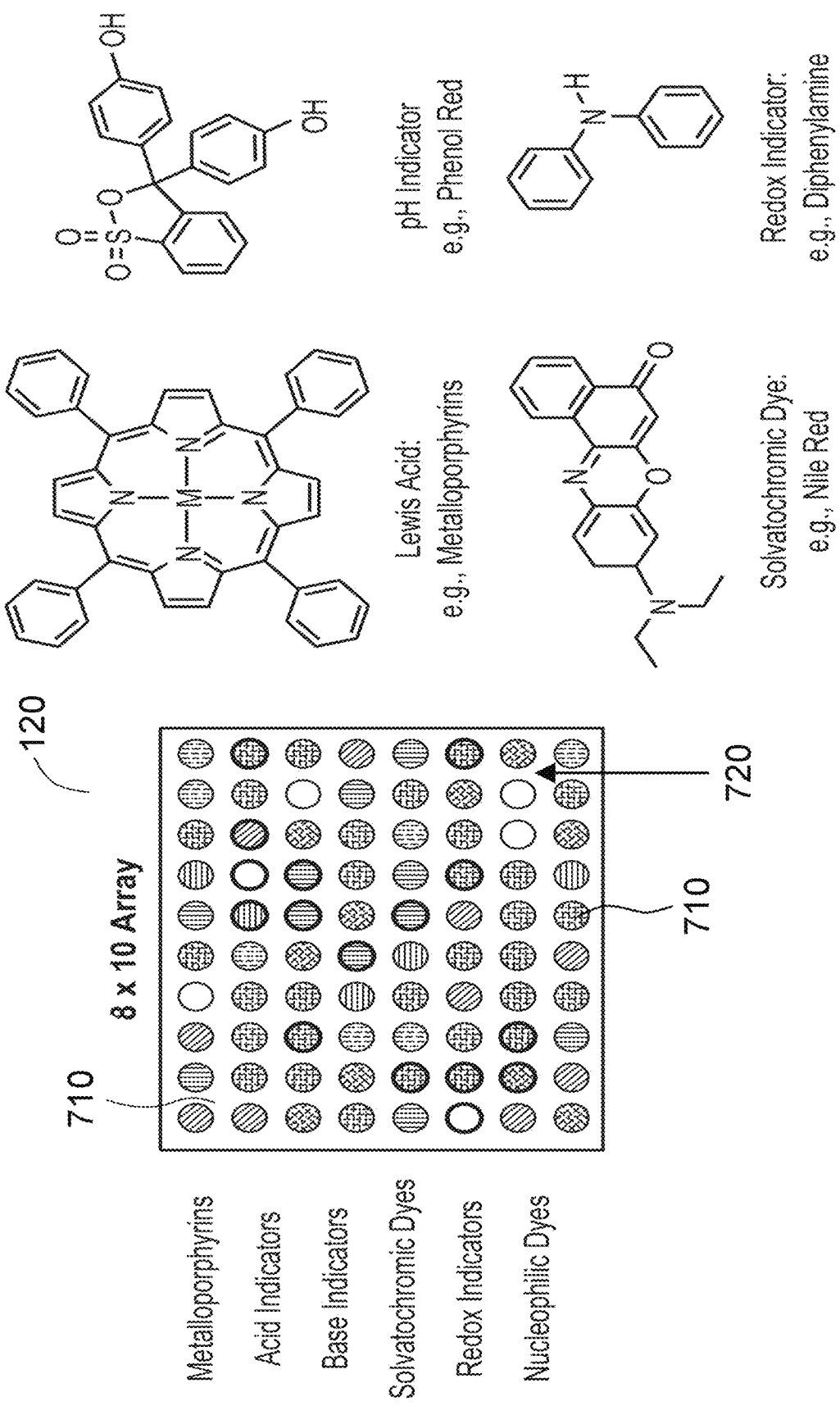
FIG. 3 depicts a diagram of an example sensor array.

FIG. 3 illustrates an embodiment of a colorimetric sensor array 120. In an embodiment, a colorimetric sensor array 120 may include a substrate 720 upon which a variety of chemically responsive indicators 710 may be deposited. The indicators 710 may change color after exposure to and reacting with volatile organic compounds. Certain indicators are responsive to certain VOCs allowing for a particular mixture of VOCs to be determined by its unique color change exhibited on the sensor array 120.

Data Processing

Data output from the detector 130 or other instruments associated with an artificial nose technology may then be stored and later processed for evaluation and diagnosis of the sample. A detector 130 may be incorporated into any suitable sensor or other instruments associated with an artificial nose technology system. The processing of the data may be performed on the processing device 140, server 150, or other computing device connected to the system. Various artificial nose technologies and systems may provide a response or an output indicative of the chemical or molecular interactions occurring at a sensor associated with the artificial nose technology. For example, many embodiments may utilize a detector 130 to detect changes after introduction of a urine sample containing VOCs.

Processing Detector Data for Colorimetric Sensor Array

In embodiments utilizing a colorimetric sensor array based artificial nose, a detector 130 may be utilized to detect optical changes in the array 120. In some embodiments, the detector 130 may only capture an image of the sensor array 120 before and at a single point in time after exposure of the indicator 710 to the sample. In other embodiments, the detector 130 may capture images at various times or continuously after exposure of the sample to the indicator 710. The color change differences before and at various points after introduction of the sample are used to classify or determine the properties of the sample. For example, when used in combination with colorimetric sensor array 120 and image analysis software, colorimetric differences can be generated by subtracting the values of indicator images generated before and after exposure of the indicator to a sample. In some embodiments, the colorimetric differences represent hue and intensity profiles for the array 120 in response to analytes contained in the sample. Thus, for each image the detector 130 may extract a 240-dimensional 16-bit vector (R, G and B values if, for example, 80 indicators are used) before and after exposure. When used in accordance with the method of the present disclosure, a unique color change signature for the sample can be created which provides both qualitative recognition and quantitative analysis of volatile organic compounds present in the sample.

Figure 4:
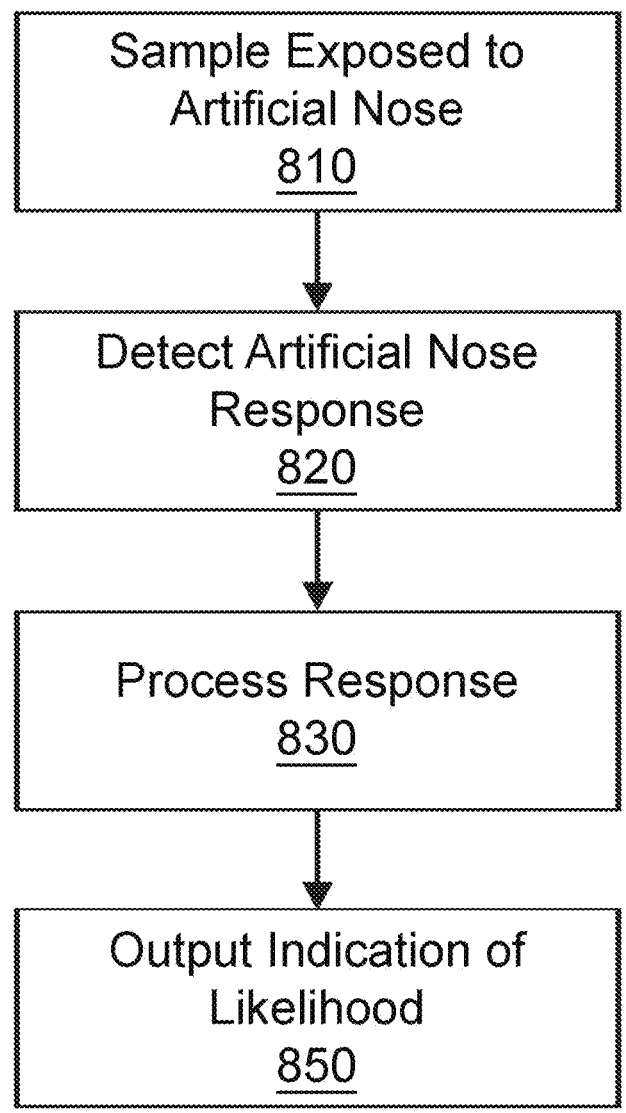
FIG. 4 depicts an example of a method determining a likelihood a patient has a malady based on detecting and processing a sensor response.

FIG. 4 illustrates an example of a process where certain or all of the steps of may be implemented or controlled by a processing device 140, detector 130, associated database 160, server 150, and other electronic components which communicate over a network. These computer or processor integrated components can automatically implement the illustrated process to provide an indication of whether a patient has lung cancer.

For example, first, a sample may be exposed to an artificial nose 810. This may be implemented by a caregiver applying a sample inside a container 200 or a processing device 140 to open a door or other feature to allow exposure of the sample to the artificial nose 810 to begin. Exposure to the sample could be performed by any suitable method that allows the headspace gas to be exposed to, come in contact with, or come within gaseous proximity to the colorimetric array 120. Next, a response or image or several responses or images as described herein of the colorimetric array or other artificial nose 820 may be captured by a detector 130. In some embodiments, the detector 130 will first capture an image or several images of the colorimetric array or artificial nose 820 as a baseline prior to exposure of the colorimetric array 120 to the sample as described herein. Particularly, responses or readings from technologies may be taken before and after introduction of the sample to the artificial nose sensor or detector 130.

Next, the system may process the image data or other artificial nose response data 830 captured by the detector 130. The processing 830 may be performed by any processing device 140 connected to the system. For example, the system may determine a colorimetric difference between the baseline image and images captured after exposure of the colorimetric sensor array 120 to the headspace gas from the sample.

Then, the system may calculate or determine what matches the response. For instance, the system may calculate or determine a likelihood a patient from which the sample came has a malady such as cancer, an infection from a microorganism, and certain information about the disease or microorganisms including its susceptibility to antibiotics based on the processing of the image or other detector 130 data. In other examples, the system may determine the likelihood the sample matches a pollutant, a chemical warfare agent, or other chemical or analyte.

For instance, this may be performed by comparing the colorimetric difference determined in the processing 830 step to a database 160 to colorimetric differences associated with samples belong to patients with known ailments such as infections from micro-organisms, cancer, or other maladies. For example, a statistical analysis may be performed using an HCA or PCA analysis (as described more fully herein) to determine the likelihood a sample indicates the associated patient has cancer, an infection, or a drug resistant infection, based on comparisons to differences in the samples in the database that are known to have lung cancer or lung cancer or based on other processing techniques that filter and identify certain features of the response.

Computer Implementation of Analysis

In order to implement the image based processing and analysis system, the system may also include a memory storage device operatively coupled to the processor that stores a multiplicity of temporal and/or static color response patterns of known species and/or strains of microorganisms (e.g., bacteria, yeast, protozoa). Thus, the system is operable to generate a temporal and/or static color response pattern of a sample, including a microorganism, and automatically identify the microorganism (e.g., by species and strain) by comparing the generated color response pattern of the array 120 with the stored multiplicity of temporal and/or static color response patterns (e.g., the "library") of known species and/or strains of microorganisms. Comparing the generated color response pattern with the library of known species and/or strains of microorganisms may be achieved by one of a number of statistical methods described herein or incorporated by reference.

In other embodiments, information output by detector 130 may be sent to a remote database to be processed and compared to a centralized database to determine the closest matching dataset. In other embodiments, certain portions of the calculation may be performed locally at a processor on the system and some portions may be performed remotely by a processor or other computing device on a server. In some embodiments, a library of datasets with previous data points for known antibiotic strains and/or known resistances or susceptibilities may be contained in the system or in a centralized server. In the server embodiments, the data could be continually updated and stored as more assays are performed and organisms identified along with susceptibilities.

The system may then output an indication of the likelihood 850 to a display associated with the system. The output of the indication may be percentage likelihood a patient has cancer, an infection, a threshold determination of whether the patient should have follow up screening or testing for cancer or infection, or further testing to validate the results or other suitable indications. The systems and methods disclosed herein may also be able to provide additional quantitative information regarding the diagnosis that may assist a patient in decision making.

Analyzing Images of Arrays

Analyzing the differences between the first image and the second image may include quantitative comparison of the digital images before and after exposure to the analyte. Using customized software or standard graphics software such as Adobe® PhotoShop®, a difference map can be obtained by subtracting the first image from the second image. To avoid subtraction artifacts at the periphery of the spots, the center of each spot can be averaged.

Figure 5C:
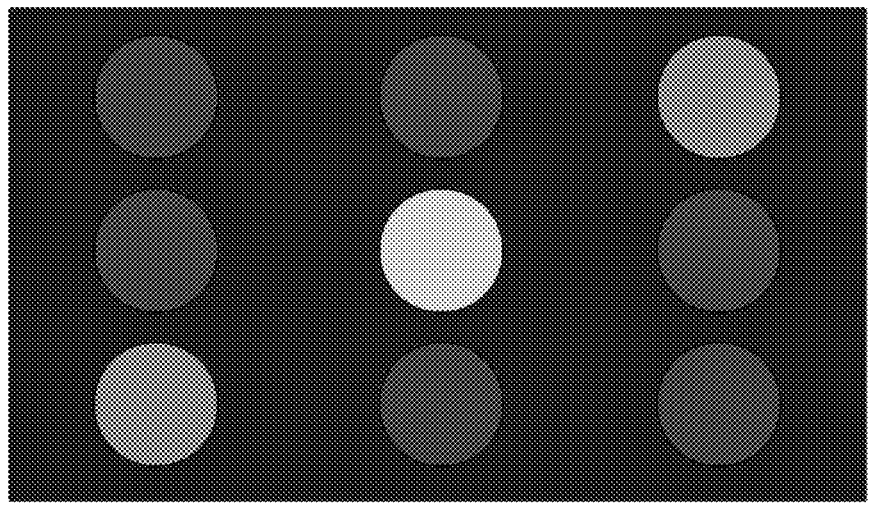
FIGS. 5A-5C depict illustrations of diagrams of an example sensor array after exposure to analytes.
Figure 5B:
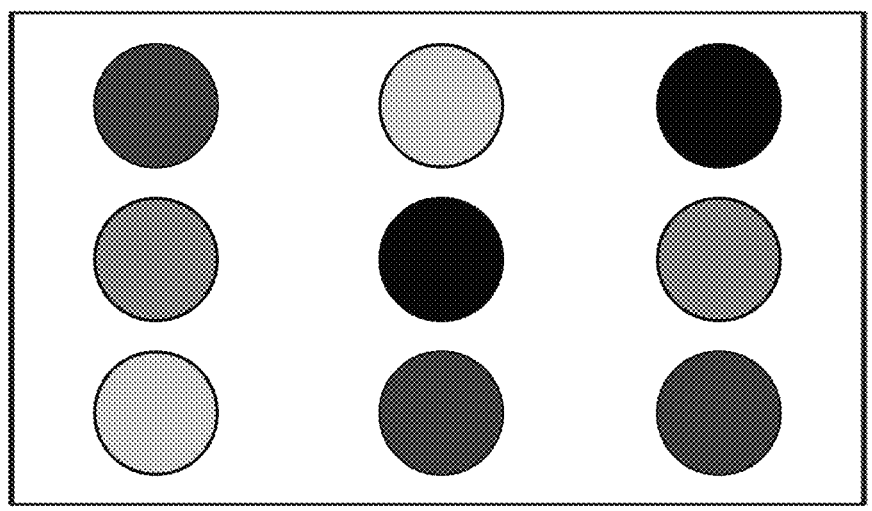
Figure 5A:
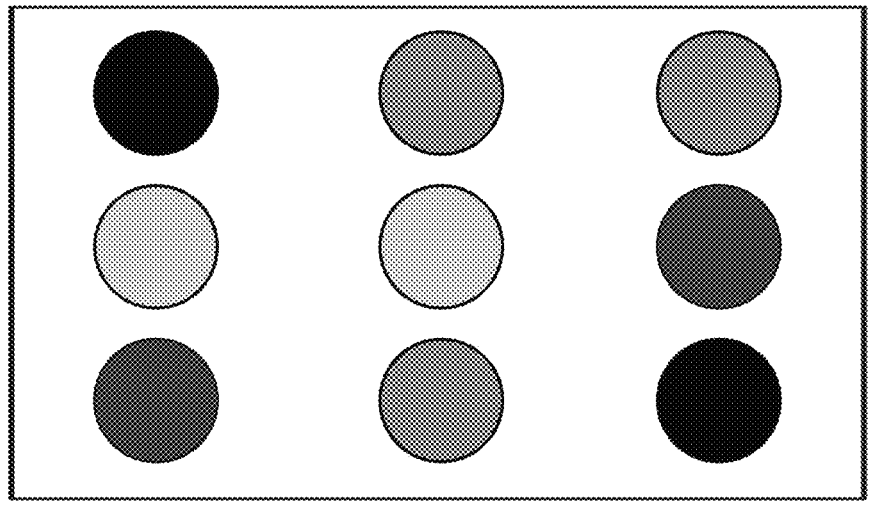

FIGS. 5A-5C are illustrations of an example image from a colorimetric sensor array, showing the array before exposure to *E. coli* ATCC 25922 (FIG. 5A), after exposure to *E. coli* ATCC 25922 (FIG. 5B), and a difference map of these two images (FIG. 5C). The comparison data obtained from the difference map includes changes in red, green and blue values ($\Delta$RGB) for each spot in the array. The changes in spectral properties that occur upon exposure to an analyte, and the resultant color difference map, can serve as a unique fingerprint for any analyte or mixture of analytes at a given concentration.

In the simplest case, an analyte can be represented by a single 3x vector representing the $\Delta$RGB values for each colorant, where x is the number of colorants as set forth in equation (1). This assumes that equilibration is relatively rapid and that any irreversible reactions between analyte and colorant are slow relative to the initial equilibration time:

$$\text{Difference vector} = \Delta R1, \Delta G1, \Delta B1, \Delta R2, \Delta G2, \Delta B2, \ldots \Delta Rx, \Delta Gx, \Delta Bx \quad (1)$$

Alternatively, the temporal response of the analyte can be used to make rapid identification, preferably using a "time-stack vector" of $\Delta$RGB values as a function of time. In equation 2, a time-stack vector is shown for an array of 36 colorants at times m, n, and finally z, all using the initial scan as the baseline for the differences in red, green and blue values:

$$\text{Time stack vector} = \Delta R1m, \Delta G1m, \Delta B1m, \Delta R2m, \Delta G2m, \Delta B2m, -\Delta R36m, \Delta G36m, \Delta B36m, \ldots \Delta R1n, \Delta G1n, \Delta B1n, \ldots \Delta R36m, \Delta G36m, \Delta B36m, \ldots \Delta R36z, \Delta G36z, \Delta B36z \quad (2)$$

Accordingly, each analyte response can be represented digitally as a vector of dimension 3xz, where x is the number of colorants and z is the number of scans at different times. Quantitative comparison of such difference vectors can be made simply by measuring the Euclidean distance in the 3xz space. Such vectors may then be treated by using chemometric or statistical analyses, including principal component analysis (PCA), hierarchical cluster analysis (HCA) and linear discriminant analysis. Statistical methods suitable for high dimensionality data are preferred. As an example, HCA systematically examines the distance between the vectors that represent each colorant, forming clusters on the basis of the multivariate distances between the analyte responses in the multidimensional ΔRGB color space using the minimum variance ("Ward's") method for classification. A dendrogram can then be generated that shows the clustering of the data from the Euclidean distances between and among the analyte vectors, much like an ancestral tree.

EXAMPLES

The following examples are provided to better illustrate the claimed invention and are not intended to be interpreted as limiting the scope of the invention. To the extent that specific materials or steps are mentioned, it is merely for purposes of illustration and is not intended to limit the invention. One skilled in the art may develop equivalent means or reactants without the exercise of inventive capacity and without departing from the scope of the invention.

Example 1

Detection of Microorganisms

Colorimetric sensor arrays described herein can be used to detect and identify pathogenic and non-pathogenic microorganisms. In one example, a sample including microorganisms from a mammal (e.g., a human) showing symptoms of a malady or in need of treatment for a malady can be taken from the mammal (e.g., in the form of a fluid sample such as blood or exhaled breath, or in the form of a tissue sample) and cultured in the presence of a colorimetric sensor array. In other examples, microorganisms such as *Saccharomyces cerevisiae* and others can be monitored in processes such as baking and alcoholic fermentation processes, electricity generation in microbial fuel cells, and biofuel production.

Response of the sensors in the colorimetric sensor array to the volatile organic compounds yields a strain-specific temporal or static color response pattern, allowing the microorganism to be identified by comparison of the color response pattern with color response patterns for known strains. Comparison may be achieved, for example, visually or automatically.

While bacteria of a given species share certain characteristics, different strains of the same species yield noticeably different color response patterns (or "fingerprints"), allowing discrimination between strains of the given species (e.g., between *Staphylococcus aureus* and methicillin-resistant *Staphylococcus aureus* and between *Enterococus faecalis* and vancomycin-resistant *Enterococus faecalis*). The color response patterns allow identification of microorganisms by species and strain and certain antibiotic resistant characteristics in a fraction of the time (e.g., about three-quarters of the time, about one-half of the time, or about one-quarter of the time) of other methods, based at least in part on conditions such as concentration, culture medium, culture conditions (e.g., temperature), and the like.

Microorganisms such as bacteria, yeasts, protozoa, and fungi can be identified as described herein. Species of bacteria that can be identified include, for example, *Staphylococcus aureus*, *Staphylococcus epidermidis*, *Staphylococcus sciuri*, *Pseudomonas aeruginosa*, *Enterococcus faecium*, *Enterococcus faecalis*, *Escherichia coli*, *Klebsiella pneumoniae*, *Streptococcus pneumoniae*, *Streptococcus pyrogenes*, *Vibrio cholera*, *Achromobacter xylosoxidans*, *Burkholderia cepacia*, *Citrobacter diversus*, *Citrobacter freundii*, *Micrococcus leuteus*, *Proteus mirabilis*, *Proteus vulgaris*, *Staphylococcus lugdunegis*, *Salmonella typhi*, *Streptococcus* Group A, *Streptococcus* Group B, *S. marcescens*, *Enterobacter cloacae*, *Bacillis anthracis*, *Bordetella pertussis*, *Clostridium* sp., *Clostridium botulinum*, *Clostridium tetani*, *Corynebacterium diphtheria*, *Moraxalla* (*Brauhamella*) *catarrhalis*, *Shigella* spp., *Haemophilus influenza*, *Stenotrophomonas maltophili*, *Pseudomonas perolens*, *Pseuomonas fragi*, *Bacteroides fragilis*, *Fusobacterium* sp. *Veillonella* sp., *Yersinia* pestis, and *Yersinia pseudotuberculosis*. Strains of bacteria that can be identified include, for example, *S. aureus* ATCC 25923, *S. aureus* ATCC 29213, *S. aureus* ATCC 43300, *S. aureus* IS-13, *S. aureus* IS-38, *S. aureus* IS-43, *S. aureus* IS-70, *S. aureus* IS-120, *S. aureus* IS-123, *S. aureus* IS-124, methicillin-resistant *S. aureus* ATCC 33591, *S. epidermidis* ATCC 35984, *S. sciuri* ATCC 49575, *P. aeruginosa* ATCC 10145, *P. aeruginosa* IS-15, *P. aeruginosa* IS-65, *P. aeruginosa* IS-22, *P. aeruginosa* IS-36, *P. aeruginosa* ATCC 27853, *E. faecium* ATCC 19434, *E. faecalis* ATCC 23241, vancoymcin-resistant *E. faecalis* ATCC 51299, *E. coli* ATCC 25922, *E. coli* ATCC 53502, *E. coli* ATCC 35218, *E. coli* ATCC 760728, *E. coli* IS-39, *E. coli* IS-44, *A. xylosoxidans* IS-30, *A. xylosoxidans* IS-35, *A. xylosoxidans* IS-46, *A. xylosoxidans* IS-55, *C. diversus* IS-01, *C. diversus* IS-28, *C. diversus* IS-31, *C. diversus* IS-33, *K. pneumoniae* IS-130, *K. pneumoniae* IS-133, *K. pneumoniae* IS-136, *K. pneumoniae* ATCC 33495, *B. anthrax* Ames, *B. anthrax* UM23CL2, *B. anthrax* V ollum, *Y. pestis* CO92, *Y. pestis* Java 9, *S. epidermis* 12228, *S. epidermis* IS-60, *S. epidermis* IS-61, *P. mirabilis* IS-18, *P. mirabilis* IS-19, *P. mirabilis* 12453, *S. marcescens* IS-48, *S. marcescens* IS-05, and *S. marcescens* 13880, where "IS-#" refers to clinical isolates and the other strains are ATCC® reference strains. Species of fungi that can be identified include, for example, *Microsporum* sp. *Trichophyton* sp. *Epidermophyton* sp., *Sporothrix schenckii*, *Wangiella dermatitidis*, *Pseudallescheria boydii*, *Madurella grisea*, *Histoplasma capsulatum*, *Blastomyces dermatitidis*, *Coccidioides immitis*, *Cryptococcus neoformans*, *Aspergillus fumigatus*, *Aspergillus niger*, and *Candida albicans*. Similarly, yeasts including Ascomycota (Saccharomycotina, Taphyrinomycotina, Schizosaccharomycetes) and Basidiomycota (Agaricomycotina, Tremellomycetes, Pucciniomycotina, Microbotryomycetes) can be identified and, if desired, assessed for susceptibility. Examples include *Saccharomyces cerevisiae* and *Candida albicans*. Protozoa including flagellates (e.g., *Giardia lamblia*), amoeboids (e.g., *Entamoeba histolytica*), sporozoans (e.g., *Plasmodium knowlesi*), and ciliates (e.g., *Balantidium coli*) may also be identified as described herein.

Arrays with Nucleophilic Indicators for Detecting Microorganisms

Nucleic indicators 710 may be beneficial for detecting microorganisms in a closed environment such as a Petri dish or blood culture bottle, as many for example many of the VOCs emitted by bacteria include ketones, aldehydes, and other molecules where concentrations of individual metabolic VOCs range from 300 to 50,000 ppb.

Example 2

Detection of Cancer

Biomarkers for cancer from blood, saliva, and urine have been identified, including the following: proteins, tumor antigens, anti-tumor antibodies, cell type-specific peptides, metabolic products and epigenetic phenomena such as hyper-methylated DNA, NRA, and the expression of specific genes. However, to date, none of these biomarkers have had the adequate sensitivity, specificity, and reproducibility to be utilized in an effective diagnostic test.

However, potential effective biomarkers for cancer may include low molecular weight volatile organic compounds, which can be detected in the urine, breath and blood of patients. This evidence for cancer metabolism is expected to manifest as a characteristic concentration profile covering dozens of metabolic VOCs. For example, the volatile organic compounds dimethyl succinate, 2-pentanone, phenol, 2-methylpyrazine, 2-hexanone, 2-butanone and acetophenone, among others, have been found in increased concentrations in the urine headspace of mice implanted with lung cancer cell lines. (Hani, et al., Analysis of volatile organic compounds released from human lung cancer cells and from the urine of tumor-bearing mice, Cancer Cell International, 2012, 12:7).

Arrays with Nucleophilic Indicators for Detecting Colon Cancer

Figure 6:
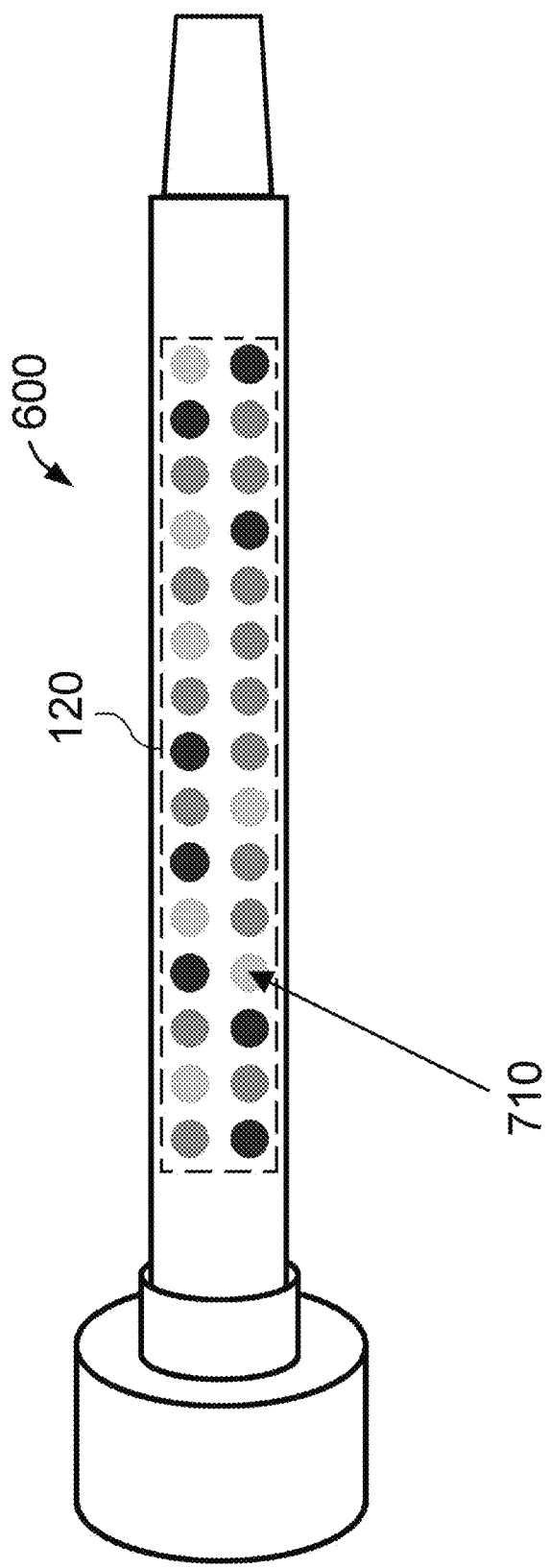
FIG. 6 depicts an example of a disposable cartridge with a sensor array inside.

As discussed herein, many of the biomarkers for cancer cells may be detected by nucleophilic indicators 710 as they are electrophilic analytes. Accordingly, a study was performed to determine whether biomarkers for colon cancer could be detected in simulated breath. FIG. 6 illustrates an example of a flow sensor 600 and sensor array 120 used to detect VOCs in a breath of a patient. In this example, the sensor array 120 included nucleophilic indicators 710. In this example, the flow sensor 600 is a linear quartz tube, and the sensor response is measured with a hyperspectral detector, that includes RGB color and four UV bands.

In this example, simulated breath with different biomarkers was pumped through the flow sensor 600. The simulated breath also contained 79% RH, 16% $O_2$ and 5% $CO_2$. Selected examples of spiked biomarkers for colon cancer include N-methylphenylethanoamine, creatine, nonanal, decanal, 4-methyl-2-pentanone, 4-methyloctane, m-xylene and p-xylene. The responses for each sensor 120 were compared before and after application of the breath. For the UV difference maps, sensor responses at three different UV bands were used to create an artificial color map.

Figure 7:
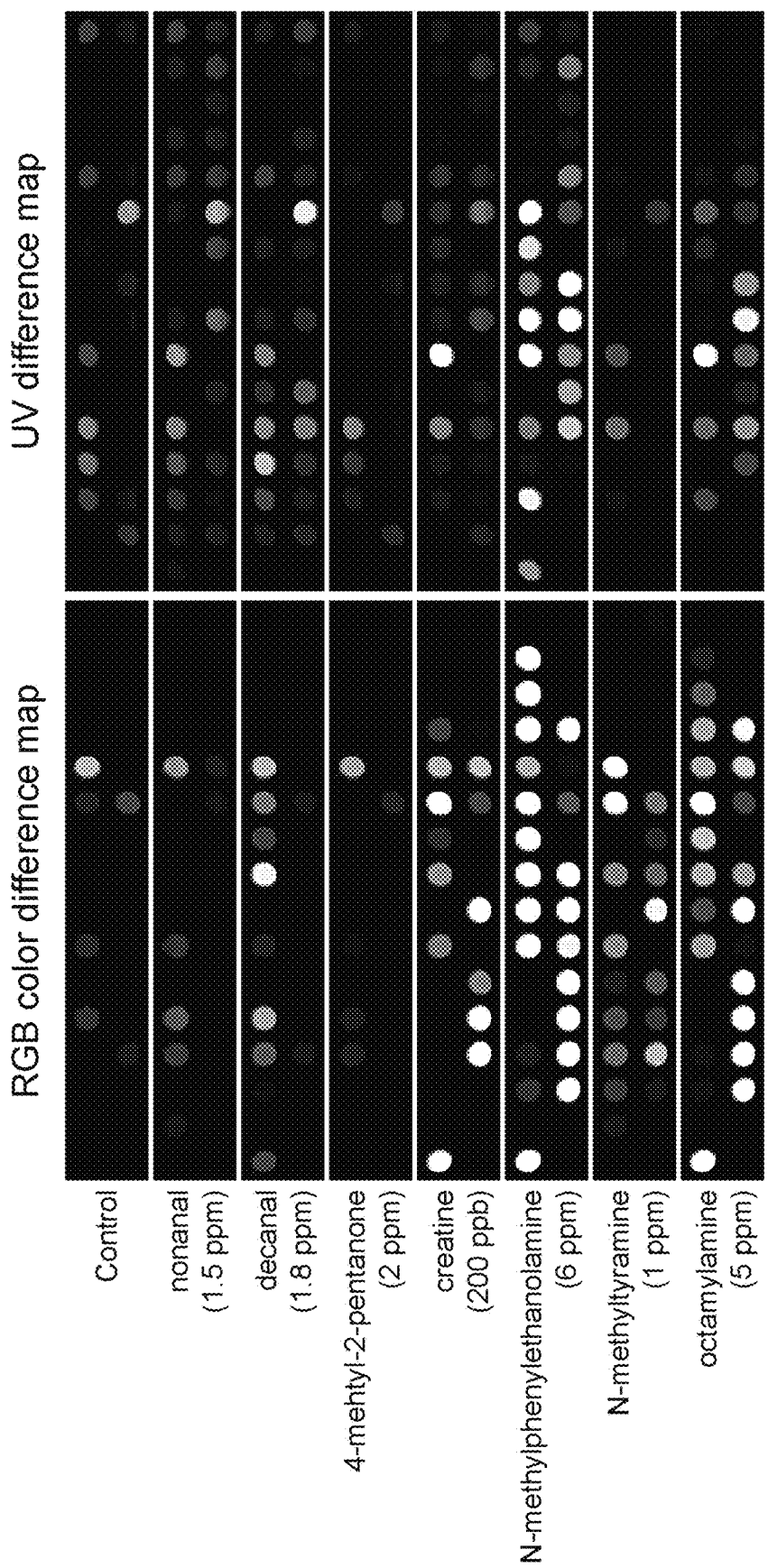
FIG. 7 depicts another example of a sensor response difference map in RGB and UV (although depicted greyscale)
Figure 8:
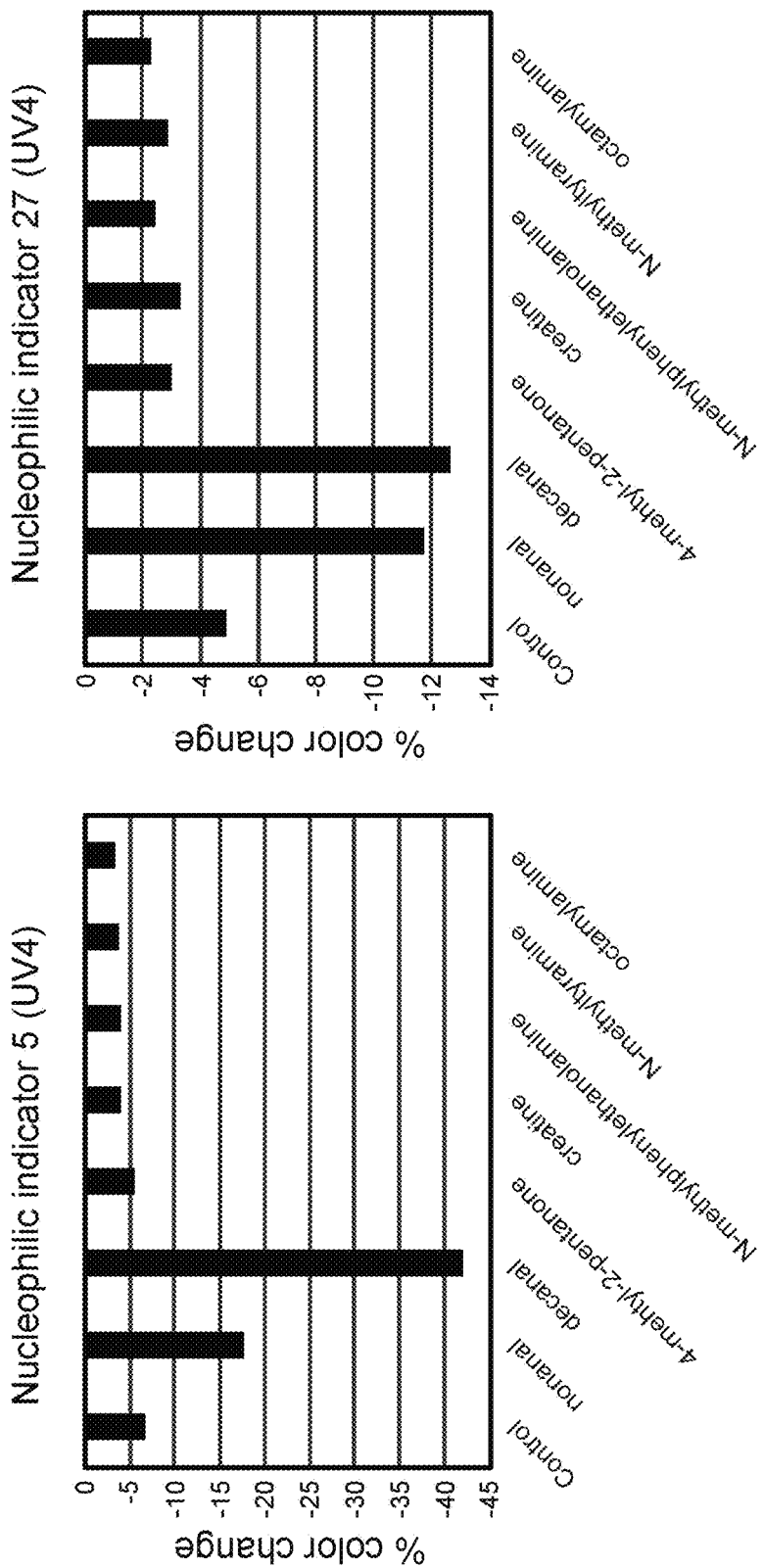
FIG. 8 depicts two bar graphs showing percentage color change of two nucleophilic indicators for various analytes.

FIG. 7 illustrates those color and UV difference maps for the different colon cancer biomarkers and a control. Those color differences are further highlighted in FIG. 8, which illustrates two bar graphs showing sensor response (color change %) for the different biomarkers. As illustrated, two of the nucleophilic indicators clearly indicated the presence of electrophilic molecules that are reported biomarkers for colon cancer. Additionally, the different responses for different nucleophilic indicators for the same two biomarkers (nonanal & decanal) indicate the surprising result. Particularly, this demonstrates that an array of more than one nucleophilic indicator could likely discriminate or identify which electrophilic analyte is present and potentially identify patients with colon cancer by sensing their exhaled breath.

In some examples, this may allow the sensor array 120 and associated system to determine which patients have cancer, and also what kind of cancer. Accordingly, a sensor with a sensor array that includes several nucleophilic indicators may be very powerful in identifying patient samples that were extracted from patients with specific types of cancers. For the aldehyde detection, o-dianisidine and 2,3-diaminonaphthalene were most effective when used with a UV reflective optical system.

Example 3

Detection of Organophosphates

Figure 9:
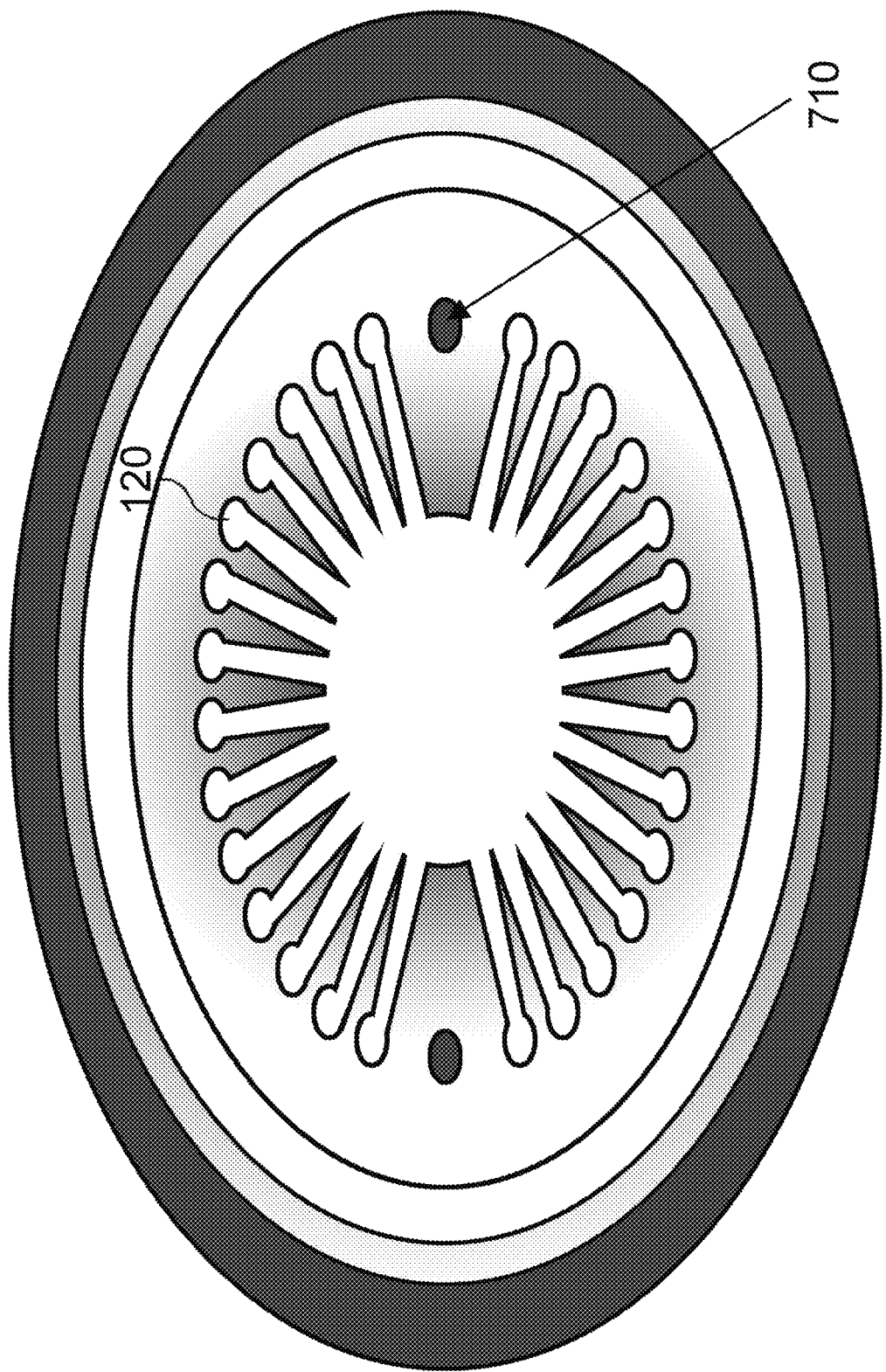
FIG. 9 depicts an example of a microfluidic cartridge with the colorimetric sensor array printed inside.

In another example, the disclosed arrays 120 with nucleophilic indicators were tested to see if they could identify organophosphates in liquid phase. FIG. 9 illustrates the array used that includes an array 120 that is liquid phase based, so it relies on capillary action for the liquid to disperse to the outside of the star and contact the indicators or dyes 710.

Figure 10:
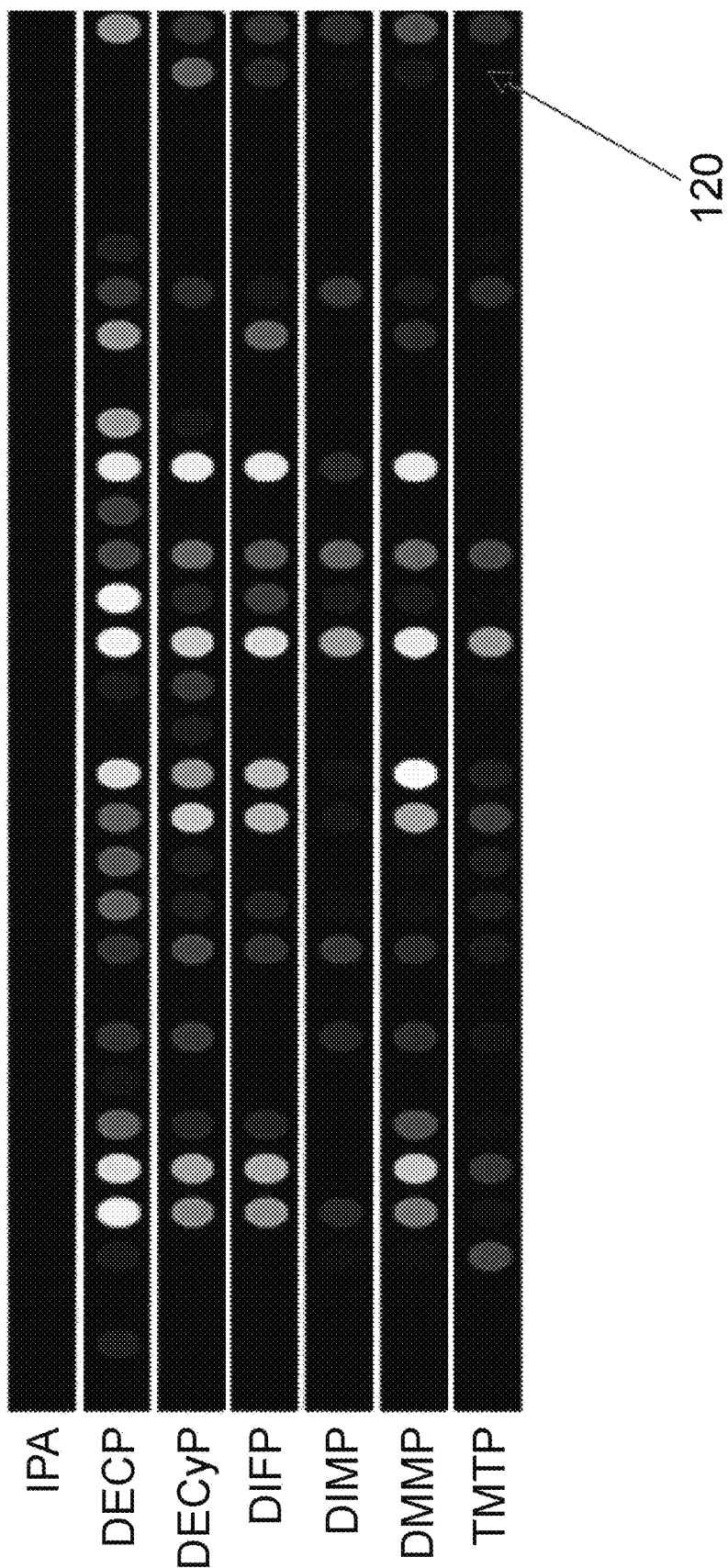
FIG. 10 depicts an example of a sensor response difference map for different liquid samples.
Figure 11:
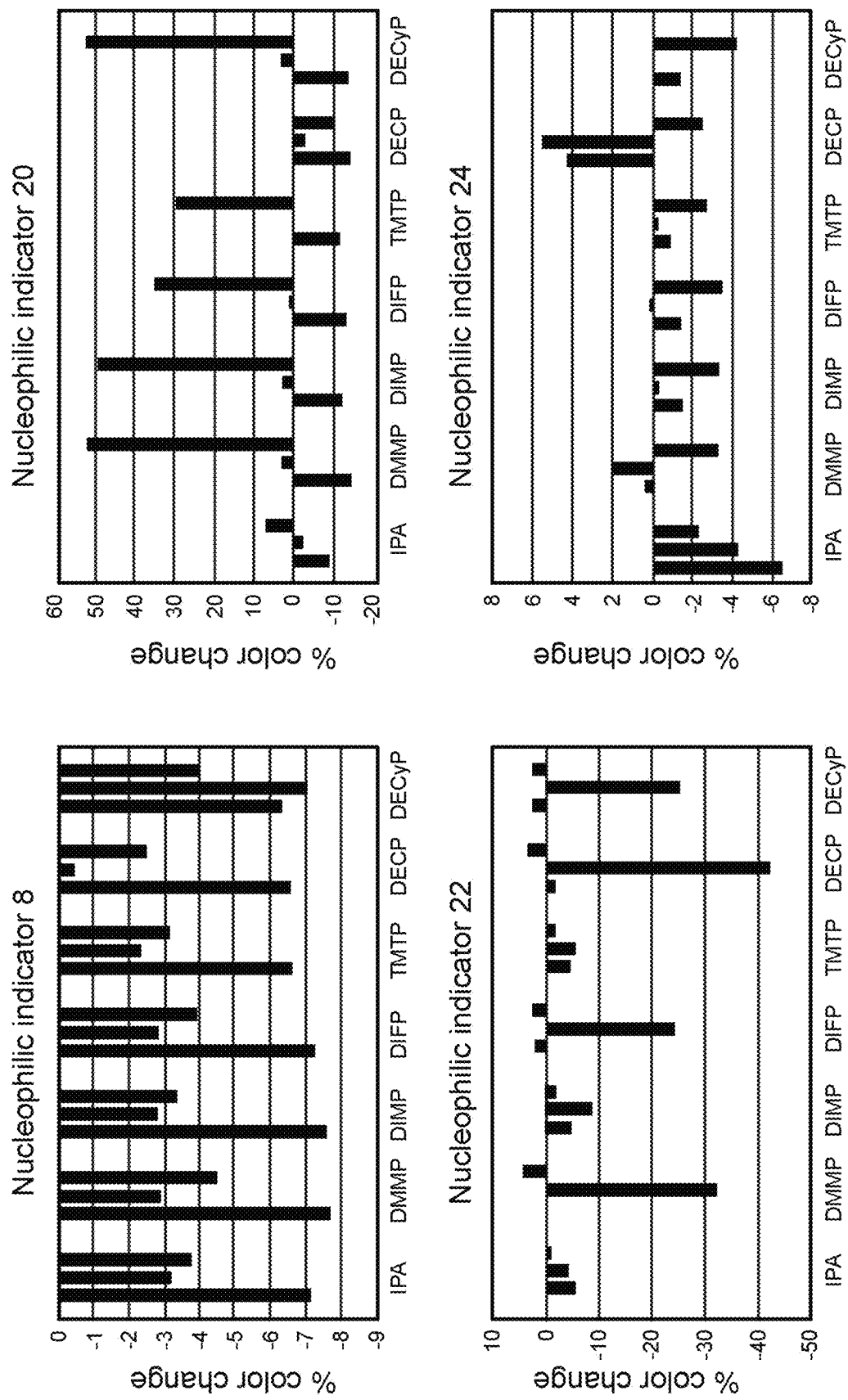
FIG. 11 depicts for bar graphs showing percentage color change to various electrophilic analytes.

FIG. 10 shows a difference map for the array 120. Those differences are further highlighted in FIG. 11, which illustrates bar graphs showing the response for four different nucleophilic indicators (indicator 8, 20, 22, and 24) included in the array 120. The results demonstrated that although indicator 8 is not effective against the six different organophosphates, the rest of the indicators show differential response to the analytes over the solvent/control (isopropanol, IPA).

Accordingly, the example illustrates the potential for a nucleophilic array to detect and potentially identify different types of organophosphate analytes. As discussed, this may be important for the detection of chemical warfare agents in the field, which could be tested with liquid based sensor arrays.

Example 4

Detection of Formaldehyde

Figure 12:
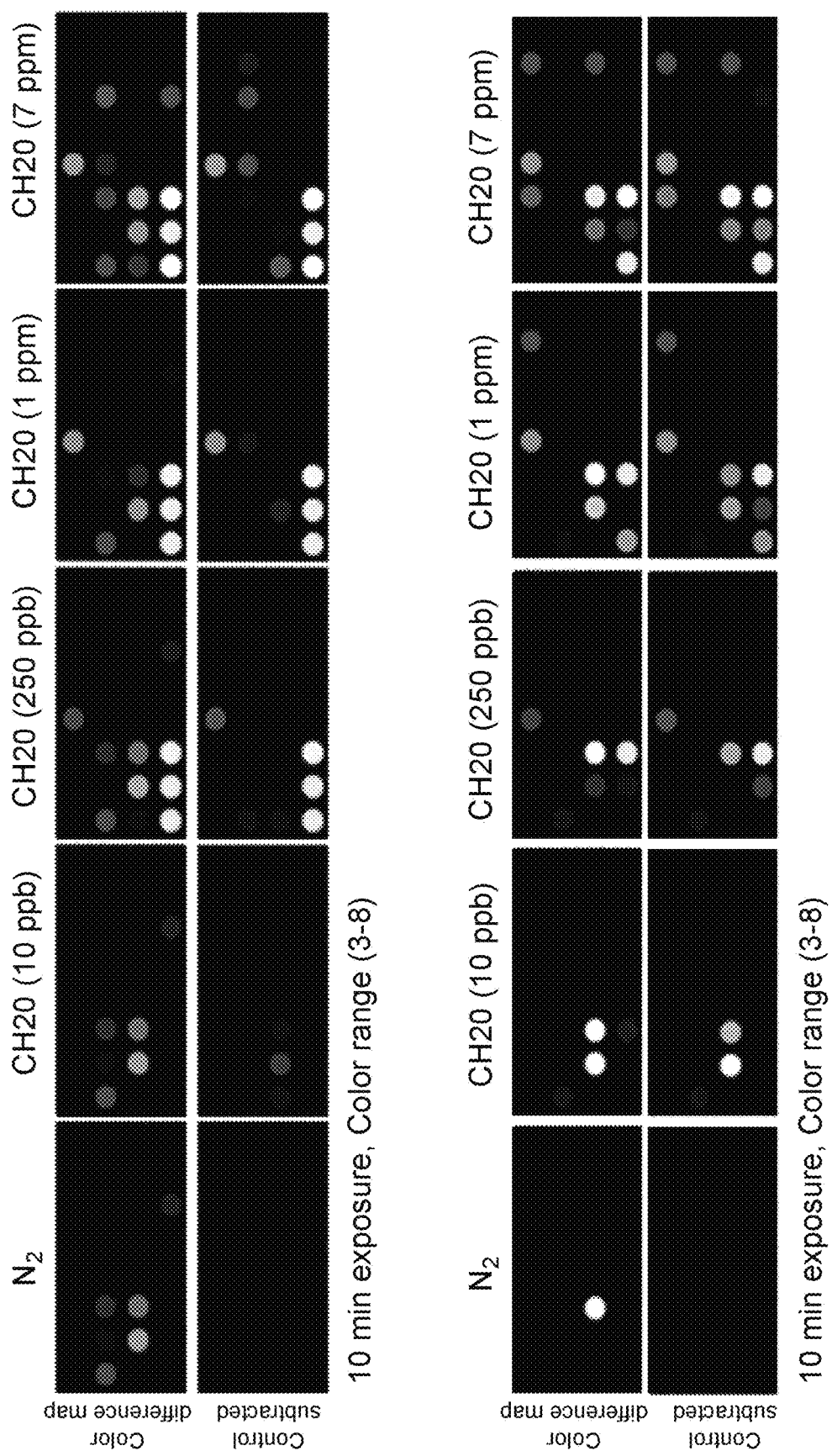
FIG. 12 depicts two example of two sensor response difference maps that were captured from sensor arrays using the same indicators on different substrates.

In another example, it was investigated whether sensor arrays with nucleophilic indicators could detect formaldehyde. FIG. 12 illustrates two color differences maps. The first map represents the results of a sensor printed on SG-81 (silica gel loaded cellulose paper) and tested against formaldehyde at different concentrations. The results show the color change after 10 minutes of exposure. The second color difference map (bottom) is captured from a sensor printed on a polypropylene membrane and tested against formaldehyde at the same concentrations.

Figure 13:
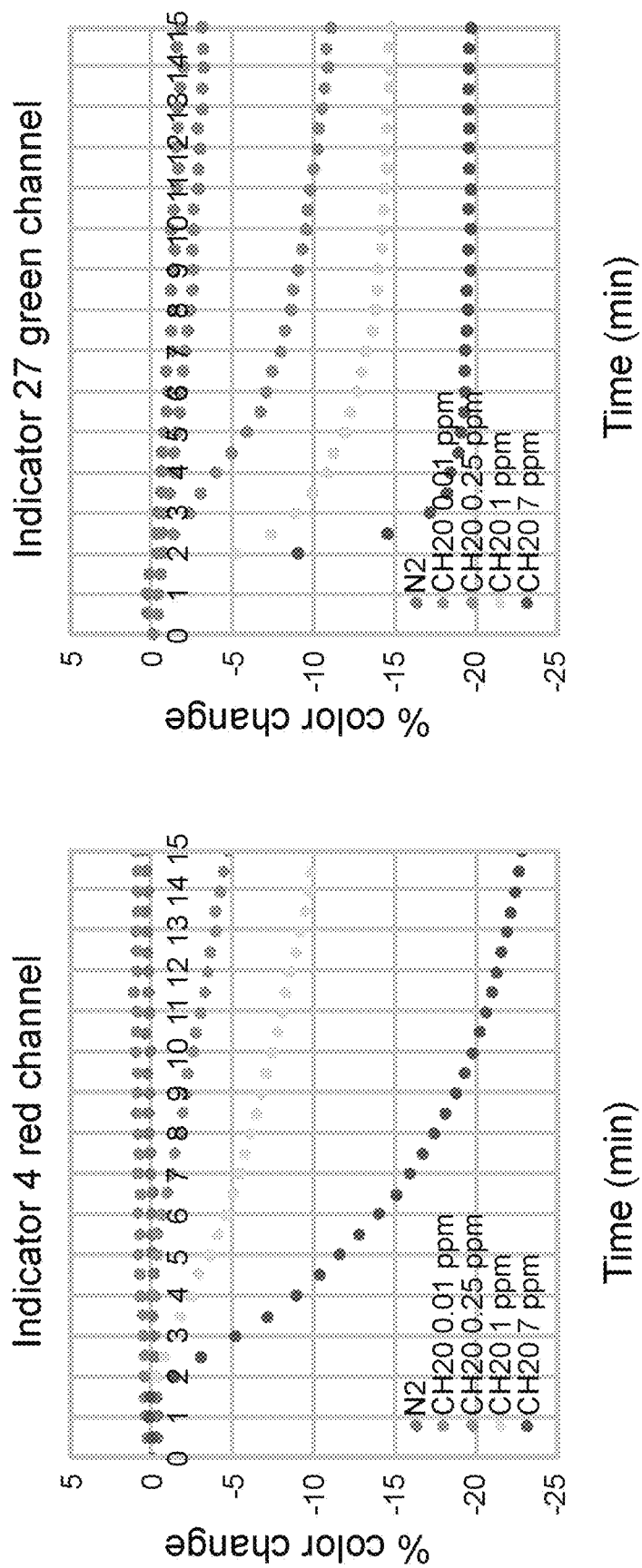
FIG. 13 depicts two graphs showing sensor response to various concentrations of formaldehyde.
Figure 14:
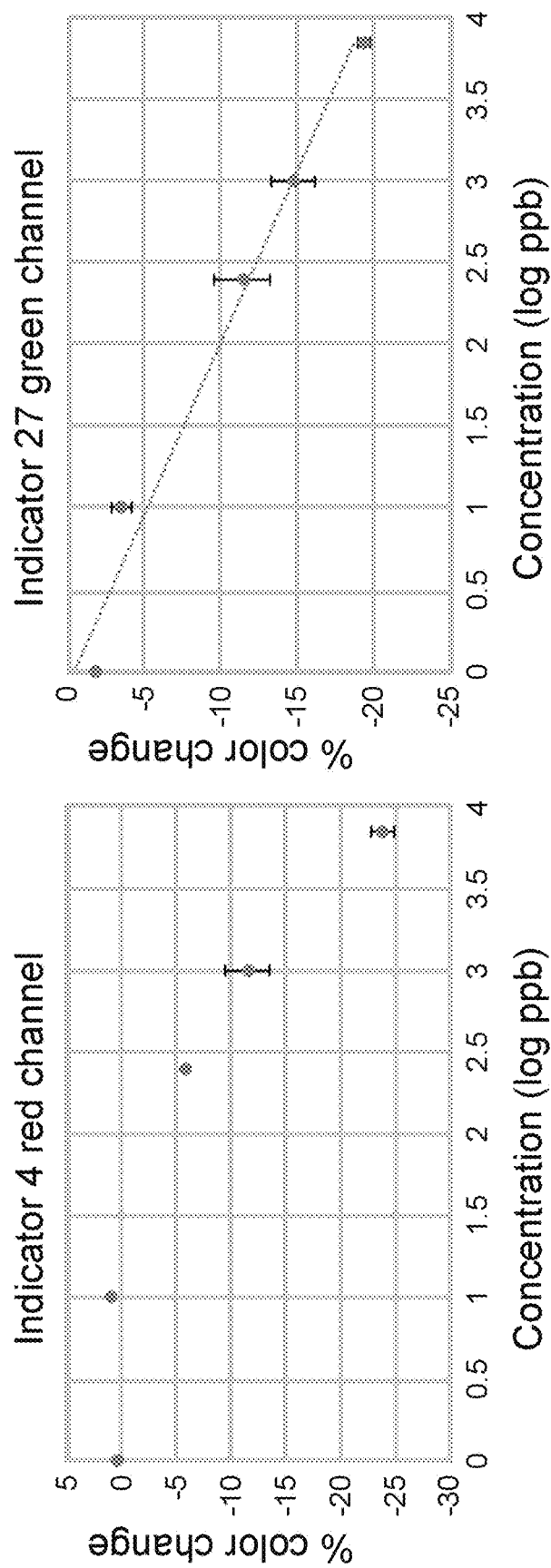
FIG. 14 depicts two graphs showing the log of the sensor response for the same data of FIG. 13.

FIG. 13 illustrates graphs of the color change response over time for two of the indicators on the SG-81 substrate 720. These graphs illustrate that the sensor can detect a response to formaldehyde even at the 10 ppb level. FIG. 14 shows a graph that is based on the log of the concentration. Accordingly, the array of nucleophilic indicators can detect formaldehyde at very low concentrations (10 ppb). With a safe exposure of 0.08 ppm, these sensors will be able to detect formaldehyde well before it becomes unsafe in the environment.

Additionally, the sensor response may be correlated to the concentration, as illustrated in FIG. 14. Accordingly, the sensor response may also be useful for determining an airborne concentration of formaldehyde, and whether the environment is safe for humans.

CONCLUSIONS

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively, or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The data processing operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of any computer programs disclosed herein include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including, by way of example, semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, certain implementations and/or portions of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Implementations of certain portions of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer to-peer networks).

Any computing systems disclosed herein can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations may be depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

The invention claimed is:

1. A sensor array comprising:
a substrate;
a first nucleophilic indicator deposited on the substrate, the first nucleophilic indicator including a parosoaniline colorant; and
a second nucleophilic indicator deposited on the substrate, the second nucleophilic indicator including an N-(rhodamine B)-deoxylactam-ethylenediamine colorant, wherein
the first nucleophilic indicator and the second nucleophilic indicator are deposited at separate locations on the substrate in a predetermined pattern,
each of the first nucleophilic indicator and the second nucleophilic indicator has a distinct spectral response to at least one distinct analyte, wherein a computer is configured to:
capture a color change of the first nucleophilic indicator over a time period and a color change of the second nucleophilic indicator over the time period, in response to the at least one distinct analyte coming in contact with both the parosoaniline colorant and the N-(rhodamine B)-deoxylactam-ethylenediamine colorant, and
compare the captured color change of the first nucleophilic indicator and the captured color change of the second nucleophilic indicator over the time period to a stored library of color response patterns to determine concentration of the at least one distinct analyte.

2. The sensor of claim 1, wherein the at least one distinct analyte is in a solution.

3. The sensor of claim 1, wherein the at least one distinct analyte is a volatile organic compound or mixtures of volatile organic compounds.

4. The sensor of claim 1, wherein the at least one distinct analyte is a cancer biomarker.

5. The sensor of claim 1, wherein the at least one distinct analyte is an aldehyde.

6. The sensor of claim 1, wherein the at least one distinct analyte is an organophosphate.

7. The sensor of claim 1, wherein the at least one distinct analyte is an electrophilic analyte.

8. The sensor of claim 1, wherein the at least one distinct analyte is a ketone.

9. The sensor of claim 1, wherein the distinct spectral response is in an ultraviolet range.

10. The sensor of claim 1, wherein a nucleophilic dye of the first nucleophilic indicator and the second nucleophilic indicator comprises at least one of the following: a plasticizer, a sol-gel, or a polymer.

11. A method for detecting an analyte comprising:
providing a sensor array comprising a first nucleophilic indicator and a second nucleophilic indicator deposited at separate locations on a substrate in a predetermined pattern, the first and second nucleophilic indicators having a distinct spectral response to at least one distinct analyte;
exposing the sensor array to the at least one analyte;
capturing, by a computer, a color change of the first nucleophilic indicator over a time period and a color change of the second nucleophilic indicator over the time period, in response to the at least one distinct analyte coming in contact with both a parosoaniline colorant in the first nucleophilic indicator and a N-(rhodamine B)-deoxylactam-ethylenediamine colorant in the second nucleophilic indicator; and
comparing, by the computer, the captured color change of the first nucleophilic indicator and the captured color change of the second nucleophilic indicator over the time period to a stored library of color response patterns to determine a concentration of the at least one distinct analyte.

12. The method of claim 11, wherein the analyte is a volatile organic compound.

13. The method of claim 11, wherein the analyte is in a solution when it is exposed to the sensor array.

14. The method of claim 11, wherein the spectral response is in an ultraviolet range.

15. The method of claim 11, wherein exposing the sensor array to the analyte comprises exposing the sensor array to a gas that contains the analyte.

16. The method of claim 15, wherein the analyte comprises a volatile organic compound.

17. The method of claim 11, wherein exposing the sensor array to the analyte comprises exposing the sensor array to a liquid that contains the analyte.

18. The sensor array of claim 1 wherein the at least one distinct analyte is formaldehyde.

\* \* \* \* \*